(12) United States Patent
Samoto et al.

(10) Patent No.: US 9,101,158 B2
(45) Date of Patent: *Aug. 11, 2015

(54) APPLICATION OF SOYBEAN EMULSION COMPOSITION TO SOYBEAN-DERIVED RAW MATERIAL-CONTAINING FOOD OR BEVERAGE

(75) Inventors: Masahiko Samoto, Osaka (JP); Jiro Kanamori, Ibaraki (JP); Norifumi Adachi, Ibaraki (JP); Chizuru Ueno, Osaka (JP); Eriko Harada, Kanagawa (JP); Mai Kanda, Osaka (JP); Takahiro Tsuruda, Saga (JP); Ayako Ogama, Osaka (JP); Yuki Usui, Ibaraki (JP); Koichi Saito, Ibaraki (JP); Kohsuke Ito, Ibaraki (JP); Hideo Sugano, Ibaraki (JP); Masashi Asanoma, Osaka (JP); Mitsutaka Kohno, Ibaraki (JP); Masayuki Shibata, Ibaraki (JP); Yuusuke Shishido, Osaka (JP); Sayuri Kitagawa, Osaka (JP); Miyuki Kanaya, Ibaraki (JP); Shigeru Ashida, Ibaraki (JP); Takayasu Motoyama, Ibaraki (JP)

(73) Assignee: FUJI OIL COMPANY LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/123,837

(22) PCT Filed: May 23, 2012

(86) PCT No.: PCT/JP2012/063110
§ 371 (c)(1),
(2), (4) Date: Dec. 4, 2013

(87) PCT Pub. No.: WO2012/169347
PCT Pub. Date: Dec. 13, 2012

(65) Prior Publication Data
US 2014/0113013 A1    Apr. 24, 2014

(30) Foreign Application Priority Data

| Jun. 7, 2011 | (JP) | 2011-126868 |
| Jun. 7, 2011 | (JP) | 2011-126871 |
| Jun. 30, 2011 | (JP) | 2011-145101 |
| Dec. 8, 2011 | (JP) | 2011-268483 |
| Dec. 8, 2011 | (JP) | 2011-268484 |
| Dec. 12, 2011 | (JP) | 2011-270814 |
| Dec. 12, 2011 | (JP) | 2011-270843 |
| Dec. 12, 2011 | (JP) | 2011-270860 |
| Dec. 12, 2011 | (JP) | 2011-271007 |

(51) Int. Cl.
*A01N 65/00* (2009.01)
*A23L 1/20* (2006.01)
*A23L 2/38* (2006.01)
*A61K 36/48* (2006.01)
*A61K 36/00* (2006.01)
(Continued)

(52) U.S. Cl.
CPC .............. *A23L 1/20* (2013.01); *A23C 11/103* (2013.01); *A23C 11/106* (2013.01); *A23C 20/025* (2013.01); *A23G 9/38* (2013.01); *A23G 9/42* (2013.01); *A23L 1/1875* (2013.01); *A23L 1/196* (2013.01); *A23L 1/2006* (2013.01); *A23L 1/24* (2013.01); *A23L 1/39* (2013.01); *A23L 2/38* (2013.01); *A23L 2/66* (2013.01); *A61K 36/00* (2013.01); *A61K 36/48* (2013.01); *A23V 2200/00* (2013.01)

(58) Field of Classification Search
CPC ................................................... A61K 36/00
USPC ............................................................ 424/725
See application file for complete search history.

(56) References Cited

U.S. PATENT DOCUMENTS

| 5,844,086 A | 12/1998 | Murray |
| 6,005,076 A | 12/1999 | Murray |

(Continued)

FOREIGN PATENT DOCUMENTS

| JP | 59-85266 | 5/1984 |
| JP | 61-3462 | 2/1986 |

(Continued)

OTHER PUBLICATIONS

International Preliminary Report on Patentability issued Dec. 10, 2013, and English translation of Written Opinion of the International Searching Authority issued Aug. 14, 2012.

(Continued)

*Primary Examiner* — Michael Meller
(74) *Attorney, Agent, or Firm* — Wenderoth, Lind & Ponack, L.L.P.

(57) ABSTRACT

The present invention addresses the problem of providing a soybean-derived raw material-containing food or beverage that improves problems with flavor and physical properties, such as the grassy smell caused by soybean raw materials, and markedly improves product quality, in a soybean-derived raw material-containing food or beverage using conventional soybean raw materials such as soymilk or tofu. Provided are a milk-substitute composition, and an egg-yolk substitute composition, etc., characterized by including a soybean emulsion composition having a protein content relative to dry material of at least 25 wt %, a fat content (as a chloroform/methanol mixed solvent extract) relative to the protein content of at least 100 wt %, and an LCI value of at least 55%. Also provided are a variety of soybean-derived raw material-containing food and beverages using these compositions.

13 Claims, 2 Drawing Sheets

(51) Int. Cl.
*A23L 2/66* (2006.01)
*A23C 11/10* (2006.01)
*A23C 20/02* (2006.01)
*A23L 1/39* (2006.01)
*A23G 9/42* (2006.01)
*A23L 1/187* (2006.01)
*A23L 1/19* (2006.01)
*A23L 1/24* (2006.01)
*A23G 9/38* (2006.01)

(56) References Cited

U.S. PATENT DOCUMENTS

| | | | |
|---|---|---|---|
| 6,548,102 | B2 | 4/2003 | Fenske et al. |
| 7,029,719 | B1 | 4/2006 | Nakajima et al. |
| 2002/0009460 | A1 | 1/2002 | Wakabayashi et al. |
| 2005/0181113 | A1 | 8/2005 | Bodor |
| 2008/0145510 | A1 | 6/2008 | Hattori |
| 2008/0213428 | A1 | 9/2008 | Sato et al. |
| 2009/0232958 | A1 | 9/2009 | Samoto et al. |
| 2010/0112187 | A1 | 5/2010 | Crank |
| 2011/0039782 | A1 | 2/2011 | Asanoma et al. |
| 2013/0078363 | A1 | 3/2013 | Samoto et al. |
| 2013/0244308 | A1* | 9/2013 | Garner et al. ............. 435/252.9 |

FOREIGN PATENT DOCUMENTS

| | | |
|---|---|---|
| JP | 61-187763 | 8/1986 |
| JP | 2-42942 | 2/1990 |
| JP | 8-298963 | 11/1996 |
| JP | 9-313101 | 12/1997 |
| JP | 11-9175 | 1/1999 |
| JP | 11-56248 | 3/1999 |
| JP | 11-506619 | 6/1999 |
| JP | 2000-102346 | 4/2000 |
| JP | 2000-279121 | 10/2000 |
| JP | 2002-209 | 1/2002 |
| JP | 2002-20781 | 1/2002 |
| JP | 2002-34503 | 2/2002 |
| JP | 2002-101820 | 4/2002 |
| JP | 2003-38096 | 2/2003 |
| JP | 2003-88334 | 3/2003 |
| JP | 2004-141155 | 5/2004 |
| JP | 2004-261107 | 9/2004 |
| JP | 2004-357522 | 12/2004 |
| JP | 2006-280310 | 10/2006 |
| JP | 2007-159593 | 6/2007 |
| JP | 2007-521824 | 8/2007 |
| JP | 2008-148633 | 7/2008 |
| JP | 2009-136158 | 6/2009 |
| JP | 2009-528847 | 8/2009 |
| JP | 2009-280517 | 12/2009 |
| JP | 2010-519928 | 6/2010 |
| JP | 2012-16348 | 1/2012 |
| WO | 97/27761 | 8/1997 |
| WO | 02/26788 | 4/2002 |
| WO | 2006/129647 | 12/2006 |
| WO | 2006/135089 | 12/2006 |
| WO | 2007/103753 | 9/2007 |
| WO | 2009/110504 | 9/2009 |
| WO | 2011/155328 | 12/2011 |

OTHER PUBLICATIONS

International Search Report issued Aug. 14, 2012 in International (PCT) Application No. PCT/JP2012/063110.

De Moura et al., "Two-Stage Countercurrent Enzyme-Assisted Aqueous Extraction Processing of Oil and Protein from Soybeans", Journal of the American Oil Chemists' Society, vol. 86, 2009, pp. 283-289.

* cited by examiner

APPLICATION OF SOYBEAN EMULSION COMPOSITION TO SOYBEAN-DERIVED RAW MATERIAL-CONTAINING FOOD OR BEVERAGE

TECHNICAL FIELD

The present invention relates to a soybean-derived raw material-containing food or beverage in which a soybean material is used as a raw material for various purposes. More specifically, the present invention relates to a soybean-derived raw material-containing food or beverage such as confectionery, bread, dessert, beverage, soup and sauce, prepared by using the soybean-derived raw material, and a production method thereof. In addition, the present invention relates to an acidic soybean material and various foods such as confectionery prepared by using the acidic soybean material. Especially, the present invention relates to the acidic soybean material suitable for a similar purpose of yogurt and cheese such as fresh cheese. In addition, the present invention relates to an egg yolk substitute composition and a food prepared by using the composition. Further, the present invention relates to a processed soy food such as tofu (bean curd), a texture improver or a taste improver for preparing a processed soy food, and a method for improving a texture or a taste of a processed soy food. Especially, the present invention relates to a processed soy food having novel texture and taste, or a processed soy food having an improved quality from a conventional product. Moreover, the present invention relates to a composition for reducing serum cholesterol or a composition for improving renal function.

BACKGROUND ART

A soybean material such as soymilk, tofu and soybean protein isolate is used as a raw material of various kind of foods or beverages, for example, a milk substitute ingredient, a substitute ingredient for fermented dairy product, an egg yolk substitute ingredient, an ingredient for processed soy food, an ingredient for reducing serum cholesterol and an ingredient for improving renal function, in a food or beverage.

A Technology Concerning a Dairy Product Substitution in a Food

For the purpose of topping (decoration), nappe (surface coating), filling or kneading in confectionery, bread, dessert or the like, and for the purpose of adding taste in cooking, fresh cream or compound cream (mixture of milk fat and vegetable fat) is widely used in order to give a peculiar rich milk taste and a cooling feel in the mouth. Especially, fresh cream is an essential material for preparing confectionery and cooking due to its full-rich taste and milk taste. However, the fresh cream is relatively expensive and difficult for long storage, for example, it is necessary to use the fresh cream within 2 or 3 days after breaking the seal even in a refrigerator, and the fresh cream does not match a health trend due to its relatively high fat content such as 30 to 50 wt % of fat content. Therefore, a fresh cream substitute material which has a good taste and good handling property is desired.

As the above mentioned substitute material, application of tofu or soymilk is considered. Although a soybean-derived raw material-containing food or beverage such as confectionery, dessert, beverage, soup and sauce has a healthful image, it has peculiar taste of raw vegetation derived from soybean and it lacks rich and delicious taste. Therefore, there are high market needs to provide a soybean-derived raw material-containing food or beverage of which such a taste is improved.

As a method for improving such a peculiar taste derived from soybean, Patent Document 1 discloses a method for reducing a taste of raw vegetation derived from soybean as well as reducing a rough texture generated in a heat treatment step by adding a low sweetness sugar composition including trisaccharide or tetrasaccharide having branching structure to a soy food or beverage. Patent Document 2 discloses a sterilized soymilk having full (rich taste) and good taste obtained by a method including acting protein cross-linking enzyme to a soymilk or a soybean raw material during a step of preparing soymilk, and then subjecting to sterilization treatment. In addition, Patent Document 3 discloses a method for producing an acidic soymilk beverage including heating soymilk at 130 to 150° C. for several tens of seconds, and then acidifying by a lactic acid fermentation or adding an acidic substance, where the obtained acidic soymilk beverage has smooth texture and rich taste without unpleasant taste such as taste of raw vegetation and harsh taste peculiar to soybean.

A Technology Concerning a Fermented Dairy Product Substitution in a Food

Next, a fermented milk obtained by lactic fermentation of milk raw material is eaten itself as cheese or yogurt, or is used as main raw material or auxiliary raw material for topping (decoration), kneading, filling or nappe (surface coating), in a processed food such as confectionery, Japanese confectionery, bread, dessert, frozen dessert and beverage.

In addition, a fermented filled milk type emulsion prepared by blending vegetable fat as substitute for milk fat while skim milk or the like is used as a milk protein, and then fermenting, is also known (Patent Documents 4 to 7). This emulsion is also used in the above mentioned processed food in the same purpose of the fermented milk, and adds various functions and additional value to the processed food to contribute to a development of food industry.

On the other hand, a fermented soybean material using a soybean protein as a protein source is expected as a plant-derived fermented material which is good for health because milk fat is not used, and a part of the material is considered as a substitute for conventional fermented dairy product such as cheese and yogurt. A soybean material such as soymilk, soybean protein isolate and soy flour is used as a raw material which contains a soybean protein.

A Technology Concerning an Egg Yolk Substitution in a Food

Next, an egg yolk is widely used to various foods such as seasoning, daily dish and confectionery because it has excellent feature in its function, nutritive value and the like. However, in recent years, an ingestion of egg yolk which has high cholesterol content tends to be avoided due to a growing awareness of health trends. Moreover, in recent years, instability of supply and rise in the price of egg etc. by the influences of a natural disaster and avian infections etc. are feared although an egg has been originally said as an "exemplary model of prices".

Various considerations concerning an egg substitute food have been conducted because of such a background. For example, an egg-like food prepared by using a dried egg white particle and dried pumpkin yellow particle, and omelet as a usage example are suggested (Patent Document 9). In addition, as a technology of using a soybean material, a technology related to a low cholesterol egg substitute composition including soybean protein and egg white protein, and baked product (pound cake) as an application example (Patent Document 10) and a technology related to an emulsion including concentrated soymilk and mayonnaise-like food as an application example prepared by using the emulsion (Patent Document 11) are disclosed. Further, a technology related to an egg substitute food prepared by using an isolated whey protein and examples of its application such as sponge cake and custard pudding are disclosed (Patent Document 12).

A Technology Concerning a Processed Soy Food

Next, tofu, yuba (bean curd skin) and abura-age (deep-fried thin bean curd) and the like, which are prepared from soybean as a raw material, are traditional processed soy foods that have long been eaten in Japan. Generally, various processed soy foods are prepared from "soymilk" as a starting raw material, where the soymilk is obtained by adding water to soybean, and then grinding to obtain "go" (soybean slurry), optionally heating the "go", and then removing okara (bean curd refuse) by centrifugation or filtration. Tofu is a typical example of the processed soy food, and various kinds of tofu are manufactured through a step of coagulating soymilk with a coagulant agent such as brine. Tofu obtained by cutting a curd which is obtained by coagulating soymilk with a coagulant agent and then immersing the cut curd in water is called as "silken tofu". In addition, tofu obtained by breaking the curd and then dehydrating and molding the curd with a filter cloth is called as "cotton tofu (firm tofu)". These tofus are comparatively firm and shape retaining gels. Recently, these tofus are marketed as filled tofu sealed in a plastic container. Although each tofu has different hardness, these tofus share an appropriate hardness and light gel texture. These traditional tofus have long been liked and are indispensable in Japanese eating habits. On the other hand, differentiated and high-value added novel tofu compared to traditional tofu is desired because the traditional tofu is cheap and has low-margin from an industrial viewpoint. Therefore, yose-tofu that a bean curd is directly put into a container without molding and thereby breaking a part of construction of curd and being indeterminate form is marketed.

In addition, it is required to develop differentiated and high-value added novel product compared to traditional product not only for tofu, but also for other processed soy foods such as abura-age, ganmodoki (deep-fried bean curd containing bits of various kinds of vegetables), atsu-age (deep-fried tofu) and yuba.

Under the circumstances, development of tofus having various kind of characteristics compared to traditional tofu has been conducted. For example, Patent Document 13 describes a tofu paste which is obtained by mixing a thickening and gelling agent, oligosaccharide and starch to tofu, mixing the mixture with high-speed cutter, heating and then cooling the mixture. In addition, Patent Document 14 describes a tofu-containing fat composition which is obtained by adding tofu which is processed to paste form into aqueous phase, and then emulsifying to water-in-oil emulsion.

Further, Patent Document 15 describes a method of producing soybean protein curd including preparing a soymilk from soybean having reduced NSI with a heat treatment, subjecting the soymilk to acidic precipitation to concentrate protein, neutralizing to re-dissolve the protein, and then adding coagulant agent and being heat-coagulated to obtain the soybean protein curd having cream-like texture.

A Technology Concerning a Reduction of Serum Cholesterol and an Improvement of Renal Function Next, there is Patent Document 16 as patent application relating to a composition for reducing serum cholesterol, where the composition is prepared from soybean as a raw material. In addition, there is Patent Document 17 as patent application relating to a powdered material for reducing blood cholesterol. Further, there is Patent Document 18 as patent application relating to a fractionated soybean protein material. Moreover, Patent Document 19 describes a soybean protein material for patients with renal disease, where the material is prepared from soybean as a raw material.

PRIOR ART DOCUMENTS

Patent Documents

Patent Document 1: JP 2006-280310 A
Patent Document 2: JP 2004-261107 A
Patent Document 3: JP 2007-159593 A
Patent Document 4: JP H11-9175 A
Patent Document 5: JP H9-313101 A
Patent Document 6: JP 2000-279121 A
Patent Document 7: JP 2004-357522 A
Patent Document 8: WO 2006/135089 A1
Patent Document 9: JP H8-298963 A
Patent Document 10: JP 2007-521824 A
Patent Document 11: JP 2002-34503 A
Patent Document 12: JP H2-42942 A
Patent Document 13: JP 2002-209 A
Patent Document 14: JP 2003-38096 A
Patent Document 15: JP S61-3462 B
Patent Document 16: JP 2003-088334 A
Patent Document 17: JP 2009-280517 A
Patent Document 18: WO 2006/129647 A1
Patent Document 19: WO 2009/110504 A1

SUMMARY OF THE INVENTION

Problems to be Solved by the Invention

An object of the present invention is to provide a soybean-derived raw material-containing food or beverage having significantly improved quality and overcoming defects relating to taste and physical property in conventional food or beverage containing soybean material such as soymilk and tofu, for example, taste of raw vegetation derived from the soybean material. Hereinafter, more specific problems will be described.

First Problem

As for the technology concerning the dairy product substitution in a food, the method disclosed in Patent Document 1 cause a feeling of strangeness between a taste peculiar to the low sweetness sugar composition and natural soybean taste. In addition, full rich taste cannot be provided by the method while a taste of raw vegetation derived from soybean can be reduced. The method disclosed in Patent Document 2 including acting protein cross-linking enzyme to a soymilk, and then subjecting to sterilization treatment can improve both taste of raw vegetation and full rich taste. However, this method has had a problem to be difficult to carry out because the method requires a delicate control of enzyme reaction condition. Further, the acidic soymilk beverage disclosed in Patent Document 3 has rich taste without taste of raw vegetation. However, there has been a problem that an intended use of the acidic soymilk beverage is limited to beverage or cooking due to its acidic taste.

As above mentioned, any conventional method cannot provide soybean-derived material having full rich taste without taste of raw vegetation derived from soybean sufficient for using as substitute for dairy product such as fresh cream.

Thus, one of the problems of the present invention is to provide a soybean-derived raw material-containing food or beverage having full rich taste without taste of raw vegetation derived from soybean by providing soybean emulsion composition which has improved flavor and can be used as a substitute for dairy product such as fresh cream, and by using the composition.

Second Problem

As for the technology concerning a fermented dairy product substitution in a food, it can be said that there have been little room in confectionery and bakery field to apply a plant-derived fermented material by substituting the soybean material for milk raw material because a preference to rich and fresh taste of milk in the confectionery and bakery field is very high. In addition, a taste of fermented soybean material itself does not show the rich and fresh taste like a milk, but tends to show unpleasant taste such as rough and astringent taste peculiar to soybean. Further, physical properties peculiar to soybean such as water retentivity and gelling property are inappropriate for physical properties of yogurt and cheese, and thereby having impact to the quality of confectionery and bread, and therefore, there is high barrier to substitute for milk material.

In order to improve the problem of the conventional fermented soybean material, various approaches have been considered, for example, masking by flavor etc., mixing with other materials, protease treatment, transglutaminase treatment, choice of lactic acid bacterium and optimization of lactic fermentation condition (Patent Document 8 etc.). However, fermented soybean material which can be used for confectionery and bakery field is still limited.

Thus, one of the problems of the present invention is to provide an acidic soybean material having a rich taste like a fermented milk or fermented filled milk type emulsion and a smooth texture without unpleasant taste peculiar to soybean.

Third Problem

As for the technology concerning an egg yolk substitution in a food, the technology disclosed in Patent Document 9 is only blending pumpkin yellow particle as substitute for the egg yolk, and cannot add required rich taste to an egg yolk substitute food. In addition, in the technology disclosed in Patent Document 10, taste of raw vegetation derived from soybean protein used as raw material may influence a taste of product. In addition, this technology may be influenced by instability of egg supply because egg white protein is essential. Further, the technology disclosed in Patent Document 11 tries to reduce an unpleasant smell of soymilk by concentrating soymilk. However, sufficient taste cannot be provided and there has been a room for improvement of quality such as rich taste of mayonnaise-like food. In the technology disclosed in Patent Document 12, there are problems of restriction in manufacturing and expensiveness because the whey protein to be used is necessary to make high purity with an adsorption resin of an ion exchange technique. Therefore, an egg yolk substitution which has rich and good taste and can be supplied at a low price is desired.

Thus, one of the problems of the present invention is to provide an egg yolk substitute composition which has rich and good taste and can be stably-supplied at a low price compared to an egg yolk, and a food using the egg yolk substitute composition.

Fourth Problem

As for the technology concerning a processed soy food, both the technologies disclosed in Patent Documents 13 and 14 use a processed material obtained by grinding tofu, which is prepared with traditional production method, to paste form. These products have taste of tofu itself and may give a coarse texture derived from tofu gel because these products are obtained only by processing tofu itself.

In addition, the soybean protein curd disclosed in Patent Document 15 requires complex processes for making a tofu-like texture to a cream-like texture and has different taste from that of natural soybean due to the acid-precipitation of soymilk.

Based on the above, one of the problems of the present invention is to provide a processed soy food having novel taste and texture differentiated from those of traditional processed soy food such as tofu or a processed soy food having improved taste and texture from a conventional processed soy food.

Fifth Problem

As for the technology concerning a reduction of serum cholesterol, one of the problems of the present invention is a composition for reducing serum cholesterol having an improved taste. As for the technology concerning an improvement of renal function, one of the problems of the present invention is a composition for improving renal function having an improved taste.

Means for Solving the Problems

As means for solving the above mentioned problems, the present invention provides the following means for solving the problems.

(1) A soybean-derived raw material-containing food or beverage comprising a soybean emulsion composition or an acidic soybean material obtained by acidification of a material comprising the soybean emulsion composition with a lactic acid fermentation or an addition of acid, wherein the soybean emulsion composition comprises a protein at a content of 25 wt % or more in terms of dry basis, and a fat at a content of 100 wt % or more (as an extract with a chloroform/methanol mixed solvent, the same will apply hereafter) relative to the protein content, and wherein the soybean emulsion composition has an LCI value of 55% or more;

(2) A soybean-derived raw material-containing food or beverage comprising the soybean emulsion composition as recited in (1) or an acidic soybean material obtained by acidification of a material comprising the soybean emulsion composition with a lactic acid fermentation or an addition of acid, wherein a fiber content of the soybean emulsion composition is 10 wt % or less and a fat content of the soybean emulsion composition is 35 wt % or more in terms of dry basis;

(3) A dairy product substitution or a fermented dairy product substitution comprising the soybean emulsion composition or the acidic soybean material as recited in (1) or (2);

(4) A soybean-derived raw material-containing food or beverage comprising the dairy product substitution or the fermented dairy product substitution according to (3) as a partial or complete substitute for dairy product or fermented dairy product;

(5) An acidic soybean material, which is obtained by acidification of the material comprising the soybean emulsion composition as recited in (1) or (2) with a lactic acid fermentation or an addition of acid;

(6) An egg yolk substitute composition comprising the soybean emulsion composition as recited in (1);

(7) An egg yolk substitute composition comprising the soybean emulsion composition as recited in (2);

(8) An egg yolk substitute food comprising the egg yolk substitute composition according to (6) or (7) as a partial or complete substitute for an egg yolk;

(9) A processed soy food comprising the soybean emulsion composition as recited in (1) as a part or all of a soybean raw material of the processed soy food;

(10) A processed soy food comprising the soybean emulsion composition as recited in (2) as a part or all of a soybean raw material of the processed soy food;

(11) A composition for reducing serum cholesterol or improving renal function, comprising the soybean emulsion composition as recited in (1);

(12) A composition for reducing serum cholesterol or improving renal function, comprising the soybean emulsion composition as recited in (2);

(13) A food comprising the composition for reducing serum cholesterol or improving renal function according to (11) or (12);

(14) A process for producing a soybean-derived raw material-containing food or beverage, which comprises using the soybean emulsion composition as recited in (1) or (2) as a substitute for a part or all of raw material selected from a group consisting of dairy product, egg yolk and soybean raw material, or as a composition for reducing serum cholesterol or improving renal function;

(15) A process for improving a taste or texture of a soybean-derived raw material-containing food or beverage, which comprises using the soybean emulsion composition as recited in (1) or (2) as a substitute for a part or all of raw material selected from a group consisting of dairy product, egg yolk and soybean raw material, or as a composition for reducing serum cholesterol or improving renal function.

Hereinafter, the soybean emulsion composition recited in the above (1) is called as "this soybean emulsion composition".

In addition, the present invention also provides more specific means for solving the problems based on the above specific first to fifth problems as follows.

First Aspect of the Invention

In order to solve the first problem relating to the technology concerning a dairy product substitution in a food, the present inventors intensively studied in order to obtain a soybean-derived material which has improved flavor and can be used as a substitute for fresh cream. As a result, they have found that an insoluble fraction obtained by water extraction of a modified soybean which is subjected to denaturation treatment to give specific NSI range is a soybean emulsion composition enriched in neutral lipid and polar lipid and is useful as a soybean-derived material having full rich taste without taste of raw vegetation derived from soybean. The first aspect of the invention has been completed on the basis of these findings.

That is, the first aspect of the invention provides the following (1) to (7):

(1) A soybean-derived raw material-containing food or beverage comprising this soybean emulsion composition;

(2) A soybean-derived raw material-containing food or beverage comprising the soybean emulsion composition as recited in (1), wherein a fiber content of the soybean emulsion composition is 10 wt % or less;

(3) A soybean-derived raw material-containing food or beverage comprising the soybean emulsion composition as recited in (1) obtained by a process comprising the step of:

i) adding water to fat-containing soybean to prepare a suspension liquid; and ii) subjecting the suspension liquid to a solid-liquid separation to transfer neutral lipid and polar lipid to an insoluble fraction, removing a soluble fraction comprising protein and sugar, and then recovering the insoluble fraction, wherein the fat-containing soybean comprises a fat at a content of 15 wt % or more in terms of dry basis and has NSI value in the range from 20 to 77;

(4) A soybean-derived raw material-containing food or beverage comprising the soybean emulsion composition as recited in (3), wherein the process further comprises homogenizing the recovered insoluble fraction, subjecting the homogenized fraction to a solid-liquid separation to remove a fiber, and then recovering a supernatant to obtain the soybean emulsion composition;

(5) Use of the soybean emulsion composition as recited in any one of (1) to (4) for a production of a soybean-derived raw material-containing food or beverage having improved taste;

(6) A process for improving taste of a soybean-derived raw material-containing food or beverage comprising using the soybean emulsion composition as recited in any one of (1) to (4) as an active ingredient for improving taste;

(7) A process for producing a soybean-derived raw material-containing food or beverage comprising using the soybean emulsion composition as recited in any one of (1) to (4) as an active ingredient for improving taste.

Second Aspect of the Invention

In order to solve the second problem relating to the technology concerning a fermented dairy product substitution in a food, the present inventors intensively studied with using a soybean material such as soymilk and soybean protein isolate as a raw material, but it has been difficult to obtain full rich taste of milk and taste with preventing unpleasant taste without adding a flavor. In addition, it has also been difficult to obtain smooth texture without adding another material such as starch and polysaccharide.

The present inventors further intensively studied in other approaches. As a result, they have found that an acidic soybean material having full rich taste and little unpleasant taste and smooth texture can be obtained by using a soybean material having a specific unique composition as a raw material. In addition, the present inventors have also found that confectionery and bread having good taste and good texture can be obtained by using the obtained acidic soybean material as substitute for fermented milk. The second aspect of the invention has been completed on the basis of these findings.

That is, the second aspect of the invention provides the following (1) to (10):

(1) An acidic soybean material, which is obtained by acidification of a raw material comprising this soybean emulsion composition with a lactic acid fermentation or an addition of acid;

(2) The material according to (1), wherein the acidic soybean material is cheese type or yogurt type;

(3) The material according to (1), wherein the acidic soybean material is whey separated type, which is obtained by separating whey after the acidification and then recovering a curd;

(4) The material according to (1), wherein the acidic soybean material is whey non-separated type, which is obtained without separation of whey after the acidification;

(5) The material according to (1), wherein the acidic soybean material is whey separated type or whey non-separated type and wherein phosphate is added to the raw material after the acidification;

(6) A food comprising the acidic soybean material according to (1);

(7) The food according to (2) comprising the acidic soybean material as a main raw material or an auxiliary raw material for kneading, filling, topping or nappe;

(8) A no-bake cheesecake-like food comprising the acidic soybean material according to (1) as a main raw material;

(9) A baked cheesecake-like food comprising the acidic soybean material according to (1) as a main raw material;

(10) A process for producing an acidic soybean material comprising acidifying a raw material comprising this soybean emulsion composition with a lactic acid fermentation or an addition of acid.

Third Aspect of the Invention

In order to solve the third problem relating to the technology concerning an egg yolk substitution in a food, the present inventors intensively studied. As a result, they have found that this soybean emulsion composition can be used for food such as seasoning, confectionery, sauce and daily dish as an egg yolk substitute composition having rich and good taste. The third aspect of the invention has been completed on the basis of these findings.

That is, the third aspect of the invention provides the following (1) to (9):

(1) An egg yolk substitute composition comprising this soybean emulsion composition;

(2) The egg yolk substitute composition according to (1) further comprising one or more material selected from a group consisting of sugar, starch, spice, fat, antioxidant and coagulant agent;

(3) The egg yolk substitute composition according to (1) or (2), wherein the egg yolk substitute composition is obtained by acting protein cross-linking enzyme;

(4) An egg yolk substitute food comprising the egg yolk substitute composition according to any one of (1) to (3);

(5) The egg yolk substitute food according to (4), wherein the egg yolk substitute food is seasoning, confectionery, sauce or daily dish;

(6) The egg yolk substitute food according to (5), wherein the seasoning is mayonnaise, dressing, baste or sauce or dried seasoning;

(7) The egg yolk substitute food according to (5), wherein the confectionery is cream, dessert or baked goods;

(8) Use of this soybean emulsion composition for an egg yolk substitute composition;

(9) A process for producing an egg yolk substitute food comprising using this soybean emulsion composition as a partial or complete substitute for an egg yolk raw material.

Fourth Aspect of the Invention

In order to solve the fourth problem relating to the technology concerning a processed soy food, the present inventors intensively studied. As a result, they have found that an insoluble fraction obtained by water extraction of a modified soybean which is subjected to denaturation treatment to give specific NSI range is a soybean emulsion composition enriched in neutral lipid and polar lipid and is useful as a soybean-derived material having full rich taste without taste of raw vegetation derived from soybean. They have also found that a processed soy food having a characteristic texture and taste and a physical property different from that of a conventional soymilk when the soybean-derived material is used as a raw material of a processed soy food by substituting it for a part or all of soymilk. The fourth aspect of the invention has been completed on the basis of these findings.

That is, the fourth aspect of the invention provides the following (1) to (7):

(1) A processed soy food comprising this soybean emulsion composition as a raw material;

(2) The processed soy food according to (1), wherein a fat content of the soybean emulsion composition is 35 wt % or more in terms of dry basis;

(3) The processed soy food according to (1), wherein a fiber content of the soybean emulsion composition is 10 wt % or less;

(4) The processed soy food according to (1), wherein a content of lipoxygenase protein relative to total protein in the soybean emulsion composition is 4% or more;

(5) The processed soy food according to (1), wherein the processed soy food is tofu, yuba, soybean seasoning, abura-age, ganmodoki or atsu-age;

(6) A texture or taste improver for producing a processed soy food, comprising this soybean emulsion composition;

(7) A process for improving texture or taste of a processed soy food, comprising using this soybean emulsion composition as a raw material.

Fifth Aspect of the Invention

In order to solve the fifth problem relating to the technology concerning a reduction of serum cholesterol and an improvement of renal function, the present inventors intensively studied.

Patent Document 16 describes that 11S globulin is assumed as an action center of reducing serum cholesterol and that a fractionation is carried out to contain a lot of 11S globulin. However, a fraction containing a lot of 11S globulin may have a taste derived from defatted soybean because the fraction is prepared from defatted soybean as a raw material in Patent Document 16.

Patent Document 17 describes a powdered material for reducing blood cholesterol. However, it is also prepared from defatted soybean as a raw material and textured process is essential feature in Patent Document 17. Therefore, the material may have a taste derived from defatted soybean and the process of preparation is complex.

Patent Document 18 also substantially discloses that defatted soybean is used as a raw material. Therefore, the obtained product may have a taste derived from defatted soybean.

In addition, Patent Document 19 describes that "non-7S and non-11S acid-precipitable soybean protein" has a strong urinary albumin lowering action. However, the "non-7S and non-11S acid-precipitable soybean protein" is prepared from defatted soybean as a raw material, and therefore, it may have a taste derived from defatted soybean.

The present inventors intensively studied in the above circumstance. As a result, they have found that an emulsion composition derived from soybean prepared by specific process has extremely good taste and strong effect of reducing serum cholesterol and improving renal function. The fifth aspect of the invention has been completed on the basis of these findings.

That is, the fifth aspect of the invention provides the following (1) to (5):

(1) A composition for reducing serum cholesterol or improving renal function, comprising this soybean emulsion composition;

(2) A composition for reducing serum cholesterol or improving renal function, comprising the soybean emulsion composition as recited in (1), wherein a fat is unrefined soybean oil;

(3) A composition for reducing serum cholesterol or improving renal function, comprising the soybean emulsion composition as recited in (1) or (2) obtained by a process comprising the step of:

i) adding water to fat-containing soybean to prepare a suspension liquid; and ii) subjecting the suspension liquid to a solid-liquid separation to transfer neutral lipid and polar lipid to an insoluble fraction, removing a soluble fraction comprising protein and sugar, and then recovering the insoluble fraction, wherein the fat-containing soybean comprises a fat at a content of 15 wt % or more in terms of dry basis and has NSI value in the range from 20 to 77;

(4) A food comprising the composition for reducing serum cholesterol or improving renal function according to (1);

(5) A process for producing a food comprising using the composition for reducing serum cholesterol or improving renal function according to (3).

Effect of the Invention

In the first aspect of the invention, this soybean emulsion composition enriched in neutral lipid and polar lipid obtained from fat-containing soybean does not have taste of raw vegetation peculiar to soybean but has full rich taste, and excellent taste of delicious taste of natural soybean. And, a soybean-derived raw material-containing food or beverage having significantly improved taste can be provided by using the soybean emulsion composition as a substitute for dairy product.

According to the second aspect of the invention, an acidic soybean material having little unpleasant taste such as degradation smell, acetic acid smell and astringency which is generated in a lactic fermentation of conventional soymilk or soybean protein isolate can be provided.

In addition, the acidic soybean material can be used for any foods for which cheese and yogurt are used, and can substitute for a part or all of cheese and yogurt.

For example, a product comparable to a no-bake cheesecake made from cheese can be prepared by using the acidic soybean material as a substitute for cheese as a main raw material. And, the no-bake cheesecake-like food having rich taste and freshness derived from soybean and smooth taste can be obtained.

In addition, novel baked cheesecake-like food having an appearance comparable to baked cheesecake made from cheese and floury sweet potato-like texture different from conventional baked cheesecake by using the acidic soybean material as a main raw material of the baked cheesecake.

According to the third aspect of the invention, an egg yolk substitute food having creamy texture and rich and good taste can be prepared by using an egg yolk substitute composition including this soybean emulsion composition.

According to the fourth aspect of the invention, full rich taste and delicious taste of natural soybean and creamy texture can be added to a processed soy food without taste of raw vegetation peculiar to soybean by using this soybean emulsion composition as a raw material of the various processed soy food, and the processed soy food differentiated from conventional product in taste and texture.

Especially, in the case of tofu or atsu-age, a product having soft and creamier texture than conventional product and good texture melting in the mouth can be obtained.

In addition, in the case of yuba, smooth texture like a fresh yuba (fresh lifted-up yuba) can be easily obtained.

Further, in the case of expanded food such as ganmodoki and abura-age, expansion of dough material in a cooking of deep-frying is more improved than conventional product, and thereby an effect of improving an expansion rate can be obtained. Moreover, absorbing amount of flavored liquid is improved and more juicy texture can be obtained by improving the expansion rate.

A composition for reducing serum cholesterol or improving renal function according to the fifth aspect of the invention has good taste and a function of reducing serum cholesterol or a function of improving renal function. Therefore, various foods having good taste and showing an effect of reducing serum cholesterol or an effect of improving renal function can be easily obtained by using the composition.

MODE FOR CARRYING OUT THE INVENTION

Figure 1:
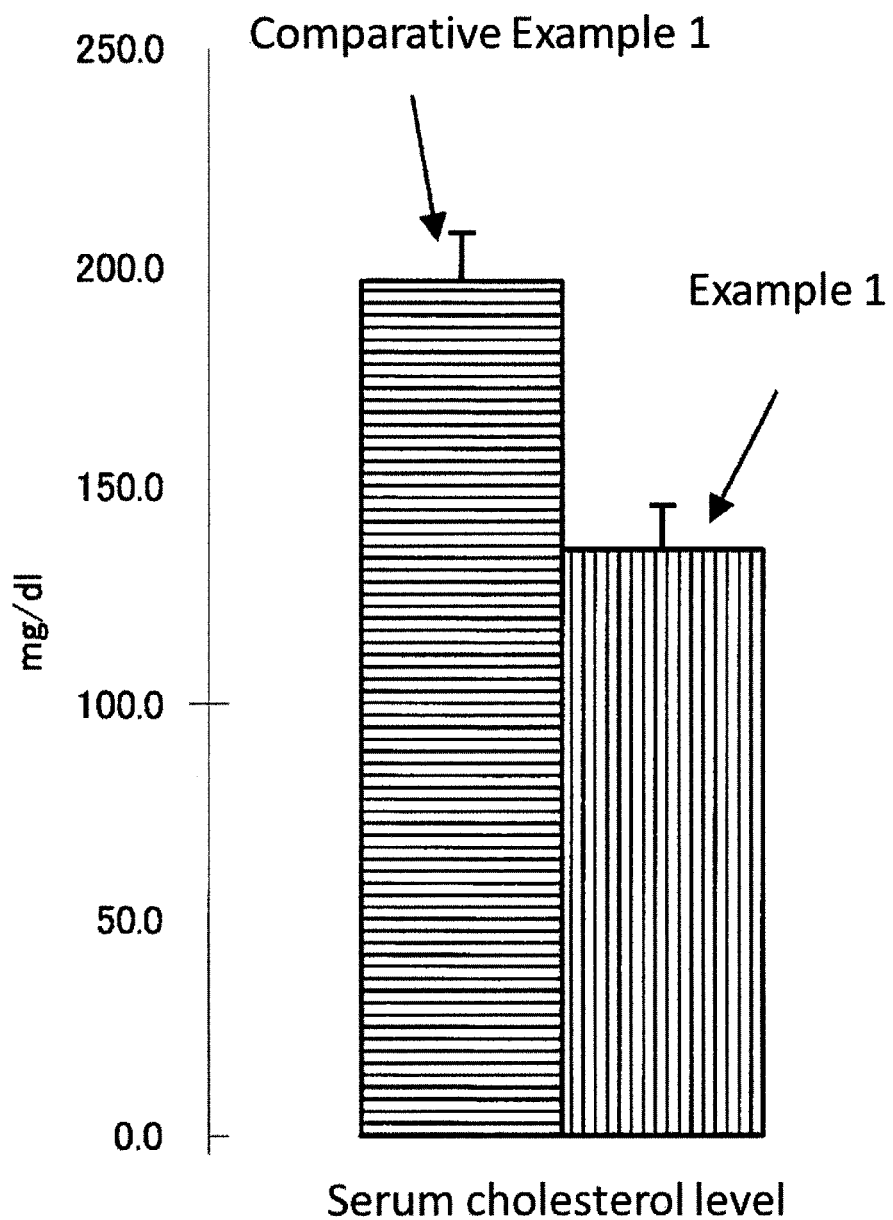
[FIG. 1] A figure showing serum cholesterol level of rat after 2 weeks feeding.
Figure 2:
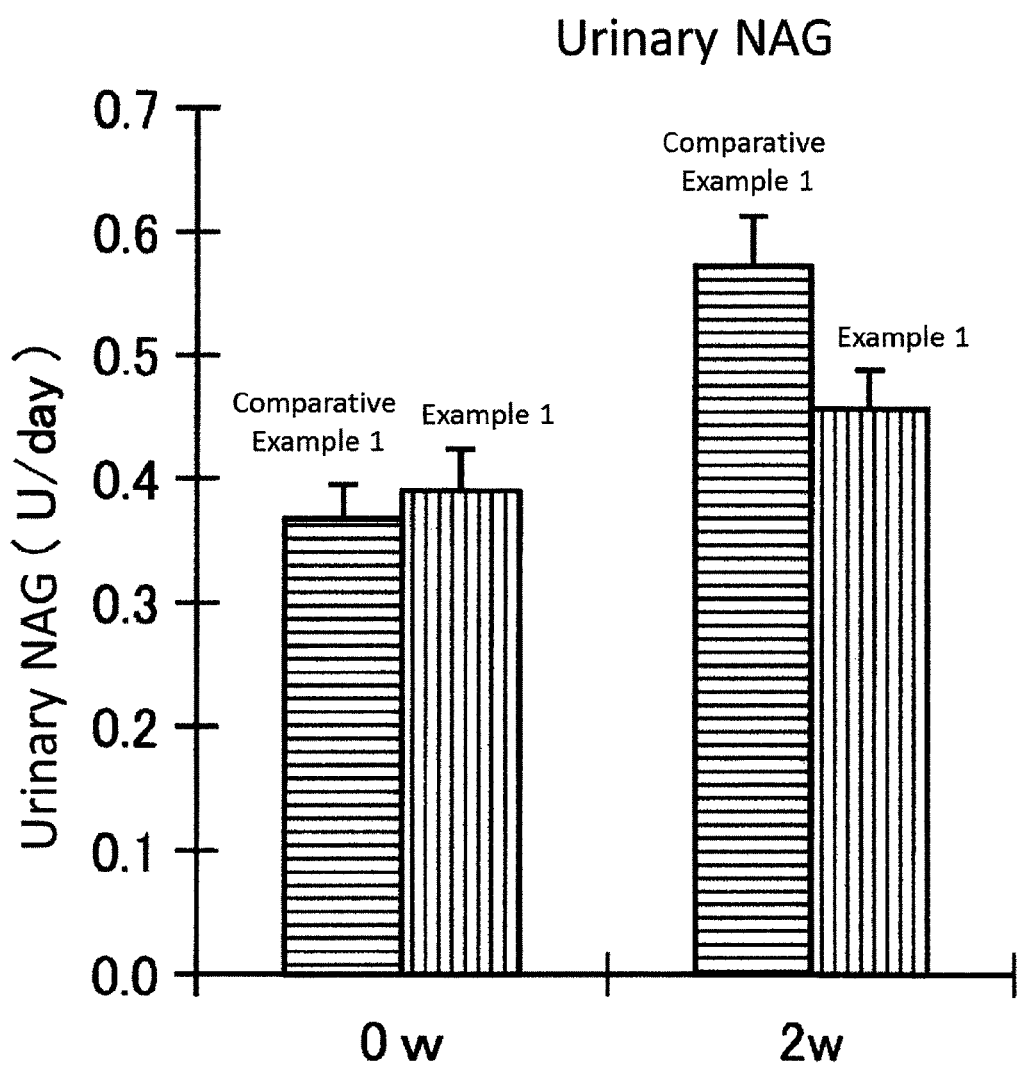
[FIG. 2] A figure showing urinary NAG activity of rat after 2 weeks feeding.

Any of a soybean-derived raw material-containing food or beverage according to the first aspect of the invention, an egg yolk substitute composition according to the third aspect of the invention, a processed soy food according to the fourth aspect of the invention and a composition for reducing serum cholesterol or improving renal function according to the fifth aspect of the invention commonly include novel "soybean emulsion composition" described in the following. In addition, an acidic soybean material according to the second aspect of the invention can be obtained by acidifying a raw material including the soybean emulsion composition with a lactic acid fermentation or an addition of acid. More specifically, a content described in the specification of Japanese patent application (Japanese patent application No. 2011-108598) is incorporated herein. Hereinafter, the soybean emulsion composition which is common specific technical feature of the first to fifth aspects of the present invention will be described.

<Soybean Emulsion Composition>

The soybean emulsion composition used in the present invention is characterized by containing neutral lipid and polar lipid at high content, wherein a ratio of lipophilic proteins (alternatively, lipoxygenase protein as another index) other than glycinin and β-conglycinin is extremely high in total protein of the composition. In addition, the soybean emulsion composition has protein content of 25 wt % or more in terms of dry basis, fat content (as an extract with a chloroform/methanol mixed solvent) of 100 wt % or more relative to the protein content in terms of dry basis, and LCI value of 55% or more, preferably 60% or more.

(Fat)

A fat content is generally determined by ether extraction method. However, this soybean emulsion composition contains not only neutral lipid but also large amount of polar lipid which is hardly extracted with ether. Therefore, a fat content of the present invention is determined by extracting with a mixed solvent of chloroform and methanol at a volume ratio of 2:1 at atmospheric boiling point for 30 minutes, and calculating fat content with assuming the obtained extract as a total fat. As a solvent extraction equipment, "Soxtec" manufactured by FOSS Co. can be used. Hereinafter, the above measurement method is also called as "chloroform/methanol mixed solvent extraction method".

This soybean emulsion composition has higher fat content than the value of fat content/protein content of soy flour. Especially, the soybean emulsion composition is rich in polar lipid. Said fat is derived from soybean as a raw material.

A fat content of this soybean emulsion composition is 100 wt % or more, preferably 120 to 250 wt %, more preferably 120 to 200 wt % or more relative to protein content in terms of dry basis, that is, fat is more than protein. When fat content is expressed as absolute amount, although it is not indispensable condition, it is preferably 35 wt % or more, more preferably 40 wt % or more in terms of dry basis. When fiber etc. is removed from the soybean emulsion composition, fat content can be 50 wt % or more in terms of dry basis. In addition, an upper limit of the fat content is, but not limited to, preferably 75 wt % or less, more preferably 70 wt % or less.
(Protein)

A protein content of this soybean emulsion composition is 25 wt % or more, preferably 30 wt % or more in terms of dry basis. In addition, an upper limit of the protein content is, but not limited to, preferably 50 wt % or less, more preferably 40 wt % or less.

Analysis of Protein Content

The protein content in the present invention is calculated by multiplying a nitrogen content measured by Kjeldahl method by a nitrogen coefficient of 6.25.

Composition Analysis of Each Component of the Protein

Each component composition of protein in this soybean emulsion composition can be analyzed by SDS polyacrylamide gel electrophoresis (SDS-PAGE). A hydrophobic interaction and a hydrogen bond between protein molecules and an intermolecular disulfide bond are broken by action of SDS as a surfactant and mercaptoethanol as a reductant, and thereby, the negatively charged protein molecule shows the electrophoresis distance according to peculiar molecular weight. In the result, an electrophoretic pattern peculiar to each protein is obtained. The analysis can be carried out by staining SDS gel with Coomassie brilliant blue (CBB) as a dye after the electrophoresis, and then calculating a proportion of density of band that corresponds to each protein molecule to density of band of total protein by using densitometry.

(Lipoxygenase Protein)

One of characteristics of this soybean emulsion composition is containing certain amount or more of lipoxygenase protein which is not generally contained in an oil body of soybean. The soybean emulsion composition contains 4% or more, preferably 5% or more of lipoxygenase protein relative to total protein in the soybean emulsion composition.

When conventional native soybean (NSI 90 or more) is used as a raw material, lipoxygenase protein is soluble and extracted to a soluble fraction after a water extraction. On the other hand, lipoxygenase is denatured by a heat treatment and insolubilized in the soybean raw material, and thereby remaining in an insoluble fraction.

By increasing lipoxygenase protein content in total protein, emulsification state of fat is stabilized, smooth texture, which is difficult to obtain from a general soybean protein composition based on globulin protein, is obtained, and rich taste is added to the soybean composition.

Normally, there are three types of lipoxygenase protein, L-1, L-2 and L-3. A content of each lipoxygenase protein can be calculated from density of band that corresponds to each lipoxygenase protein by using the above electrophoresis.

(Lipophilic Proteins)

One of characteristics of this soybean emulsion composition is containing lipophilic proteins among several kind of protein at higher content as compared with conventional soybean composition.

The lipophilic proteins refer to a group of minor acid-precipitable soybean proteins other than glycinin (7S globulin) and β-conglycinin (11S globulin) among acid-precipitable soybean proteins of a soybean, and are accompanied by a lot of polar lipids such as lecithin and glycolipid. Hereinafter, the lipophilic proteins are simply abbreviated as "LP" in some cases.

Since LP is a mixture of various proteins, it is difficult to specify all of respective proteins and LP content. However, LP content can be estimated by determining the following LCI (Lipophilic Proteins Content Index) value. LCI value of protein in the soybean emulsion composition is usually 55% or more, preferably 58% or more, more preferably 60% or more, further preferably 63% or more, most preferably 65% or more.

When conventional native soybean (NSI 90 or more) is used as a raw material, LP is soluble and extracted to a soluble fraction after a water extraction. On the other hand, LP is denatured by a heat treatment and insolubilized in the soybean raw material, and thereby remaining in an insoluble fraction.

By increasing LP content in total protein, emulsification state of fat is stabilized, smooth texture which is difficult to obtain from a general soybean protein composition based on globulin protein is obtained, and rich taste is added to the soybean composition.

Method of Estimating LP Content and Measuring LCI Value (a) As the main proteins in respective proteins, an α subunit and an α' subunit (α+α') are selected for 7S, an acidic subunit (AS) is selected for 11S, and a 34 kDa protein and lipoxygenase (P34+Lx) are selected for LP. Then, a staining ratio among the selected proteins on SDS-PAGE is determined. Electrophoresis can be performed under the condition shown in Table 1.

(b) $X(\%)=(P34+Lx)/\{(P34+Lx)+(\alpha+\alpha')+AS\}\times 100(\%)$ is calculated.

(c) Since the LP content of an isolated soybean protein prepared from a low-denatured defatted soybean is about 38% as measured by the fractionation methods of the above described Methods 1 and 2 before heat-sterilization, (P34+Lx) is multiplied by a correction coefficient $k^*=6$ so that X becomes 38(%).

(d) That is, an estimated LP content (Lipophilic Proteins Content Index, hereinafter abbreviated as "LCI") is calculated by the equation below.

TABLE 1

| | |
|---|---|
| Application amount: | 10 μl of a protein 0.1% sample solution per well |
| Well width: | 5 mm |
| Well volume: | 30 μl |
| Staining solution: | Coomassie Brilliant Blue (CBB) 1 g, methanol 500 ml, glacial acetic acid 70 ml (after CBB is completely dissolved in methanol, acetic acid and water are added to 1 L) |
| Staining time: | 15 hours |
| Discoloration time: | 6 hours |
| Densitometer: | GS-710 Calibrated Imaging Densitometer/Quantity One Software Ver.4.2.3 (Bio Rad Japan Co. Ltd) Scanning width: 5.3 mm, Sensitivity: 30 |

$$LCI(\%) = \frac{k^* \times (P34 + Lx)}{k^* \times (P34 + Lx) + (\alpha + \alpha') + AS} \times 100$$

K*: Correction coefficient (6)
P34: LP main component, 34 kDa protein
Lx: LP main component, lipoxygenase
α: 7S main component, α subunit
α': 7S main component, α' subunit
AS: 11S main component, acidic subunit
(Dry Matter)

Generally, a form of this soybean emulsion composition of the present invention is similar to that of fresh cream. Dry matter in the soybean emulsion composition is usually, but not limited to, around 20 to 30 wt %. For example, the soybean emulsion composition can be a liquid form with low viscosity obtained by adding water, a cream form with high viscosity obtained by condensation and a powder form obtained by powderization.

(Aspect of Producing the Soybean Emulsion Composition)

This soybean emulsion composition can be obtained by adding water to a fat-containing soybean which contains a fat at a content of 15 wt % or more in terms of dry basis and which has Nitrogen Solubility Index (hereinafter, refers to "NSI") in the range from 20 to 77, preferably from 20 to 70, to prepare a suspension liquid, and then subjecting the suspension liquid to a solid-liquid separation to transfer neutral lipid and polar lipid to an insoluble fraction, and then removing a soluble fraction including protein and sugar, and then recovering the insoluble fraction. Hereinafter, an aspect of the production method will be explained.

Soybean Raw Material and Processing thereof

A fat-containing soybean such as whole fat soybean, partially defatted soybean is used as soybean raw material for producing this soybean emulsion composition. The partially defatted soybean includes one obtained by subjecting whole fat soybean to a physical extraction treatment such as press extraction for partially defatting. Generally, whole fat soybean contains about 20 to 30 wt % of fat in terms of dry basis. There are also special soybeans which contain 30 wt % or more of fat. The fat-containing soybean used for the present invention is not limited, but soybean having 15 wt % or more, preferably 20 wt % or more of fat is preferable. A form of the raw material can include halved, grits or powder form.

When fat content is too low because of too much defatting, it is difficult to obtain the soybean emulsion composition rich in fat of the present invention. Especially, defatted soybean having 1 wt % or less of neutral lipid content obtained by solvent extraction such as hexane extraction is not preferable because good soybean taste is deteriorated.

Generally, the above described fat-containing soybean is soluble and has 90 or more of NSI because most of the constituent proteins are nature and soluble. However, a modified soybean, which is subjected to a process so that NSI of the modified soybean is 20 to 77, preferably 20 to 70, is preferable. A lower limit of the NSI is more preferably 40 or more, further preferably 41 or more, further more preferably 43 or more, most preferably 45 or more. An upper limit of the NSI is more preferably less than 75, further preferably less than 70. In addition, soybean having low NSI such as less than 65, less than 60 and less than 58 can be used.

Such a modified soybean is obtained by carrying out a processing treatment such as heat treatment and alcohol treatment. The processing treatment includes, but not limited to, heat treatment such as dry heat treatment, steam treatment, superheated steam treatment and microwave treatment, hydrous ethanol treatment, high-pressure treatment and combination thereof.

When NSI is too low, protein ratio in the soybean emulsion composition tends to be high, that is, fat content relative to protein content becomes low. In addition, unpleasant taste such as roast flavor tends to be added. On the other hand, when NSI is high value such as 80 or more, protein ratio in the soybean emulsion composition is low and fat recovery rate from soybean also tends to be low. In addition, as for the taste, taste of raw vegetation becomes strong.

When heat treatment with superheated steam is carried out, treatment condition cannot be specified for all cases since it will differ depending on manufacturing environment, but appropriate condition for obtaining a modified soybean having the above range of NSI can be determined without special difficulty, for example, heating with superheated steam at about 120 to 250° C. for 5 to 10 minutes. As simple means, commercially available soybean having the above range of NSI can be used.

NSI can be expressed as ratio (wt %) of water-soluble nitrogen (crude protein) to total protein and determined by a prescribed method. In the present invention, NSI is determined by the following method.

To 2.0 g of sample is added 100 ml of water. The mixture is stirred at 40° C. for 60 minutes, and then centrifuged at 1400×g for 10 minutes to obtain supernatant 1. To the residual precipitate is added 100 ml of water. The mixture is stirred at 40° C. for 60 minutes, and then centrifuged at 1400×g for 10 minutes to obtain supernatant 2. The supernatant 1 and supernatant 2 are combined, and water is added to 250 ml. After filtering the mixture with No. 5A filter paper, nitrogen in the filtrate is determined by Kjeldahl method. At the same time, nitrogen in the sample is determined by Kjeldahl method. NSI is the ratio of nitrogen in the filtrate (soluble nitrogen) to total nitrogen in the sample, and expressed as wt %.

The above modified soybean is preferably subjected to a dry or wet tissue destruction treatment such as grinding, crushing and depressing before a water extraction. The soybean can be swelled by water immersion or steaming before the tissue destruction treatment. By the swelling, the amount of energy required to the tissue destruction can be reduced and component having unpleasant taste such as whey protein and oligosaccharide can be eluted and removed, as well as, extraction ratio of globulin protein (in particular, glycinin and β-conglycinin) having high water retention ability and gelling ability to total protein can be increased, that is, transfer ratio of the globulin protein into the soluble fraction can be increased.

Water Extraction from Soybean Raw Material

Water extraction is carried out by adding water at about 3 to 20 times by weight, preferably 4 to 15 times by weight relative to an amount of fat-containing soybean, and thereby preparing a suspension of the fat-containing soybean. When adding ratio of water is high, extraction rate of water-soluble component is high and good separation can be obtained. But, when the adding ratio is too high, a concentration is necessary and thereby increasing in cost. In addition, when water extraction is repeated twice or more, extraction rate of water-soluble component can be improved.

An extraction temperature is not limited. When the temperature is high, an extraction rate of water-soluble component can be improved, but fat also tends to be soluble, and thereby, fat content in the soybean emulsion composition becomes low. Therefore, the extraction temperature is preferably 70° C. or lower, more preferably 55° C. or lower. Alternatively, the water extraction can be carried out at 5 to 80° C., more preferably 50 to 75° C.

Concerning an extraction pH (pH of a soybean suspension after adding water), as is the case in the extraction temperature, when the pH is high, an extraction rate of water-soluble component can be improved, but fat also tends to be soluble, and thereby, fat content in the soybean emulsion composition becomes low. On the other hand, when the pH is too low, an extraction rate of protein tends to be low. More specifically, the extraction can be carried out with adjusting a lower limit of pH to pH 6 or higher, pH 6.3 or higher, or pH 6.5 or higher. In addition, the extraction can be carried out with adjusting an upper limit of pH to pH 9 or lower, pH 8 or lower, or pH 7 or lower from a standpoint of increasing a separation efficiency of fat. Alternatively, the extraction can be carried out with adjusting pH to more alkaline, pH 9 to 12 from a standpoint of increasing an extraction rate of protein.

Solid-liquid Separation after the Water Extraction

After the water extraction, suspension of the fat-containing soybean is subjected to a solid-liquid separation such as centrifugation and filtration. In this case, it is important that most of fat including neutral lipid as well as polar lipid is not eluted to water-extract, but transferred to a fraction of insolubilized protein and fiber as a precipitate (insoluble fraction). More specifically, 70 wt % or more of fat of fat-containing soybean is transferred to the precipitate. In addition, a small amount of fat is eluted to a supernatant when carrying out the extraction. However, it is different from a fat which is finely emulsified in soymilk, and can easily be floated and separated by centrifuging at 15,000×g or less or about 5,000×g or less. In this respect, it is preferable to use a centrifuge. In addition, an ultracentrifuge at 100 thousand×g or more can be used depending on facilities. However, in the case of this soybean emulsion composition used in the present invention, it can be carried out without using the ultracentrifuge.

In addition, demulsifier can be added during or after the water extraction to improve fat separation from soymilk. The demulsifier is not limited, for example, a demulsifier described in Patent Document 2 described in the specification of Japanese patent application (Japanese application No. 2011-108598) can be used. Further, the present invention can be carried out without using the demulsifier.

Not only neutral lipid but also polar lipid can be transferred to an insoluble fraction by the solid-liquid separation after the water extraction. A fraction of this soybean emulsion composition can be obtained by recovering the fraction.

In the case of using centrifugation as solid-liquid separation, both two phase separation system and three phase separation system can be used. In the case of using the two phase separation system, an insoluble fraction as precipitate layer is recovered. In the case of using the three phase separation system, it can be separated to three fractions, (1) floating layer (cream fraction with lowest specific weight including fat), (2) mid layer (water-soluble fraction including a small amount of fat and large amounts of protein and sugar) and (3) precipitate layer (insoluble fraction including large amounts of fat and fiber). In this case, soluble fraction, mid layer (2) is removed or recovered, and floating layer (1) or precipitate layer (3) is recovered. Alternatively, floating layer (1) and precipitate layer (3) are recovered in combination.

The obtained insoluble fraction (1) and (3) can be this soybean emulsion composition as is, or after subjecting to concentration step, heat pasteurization step and powderization step as necessary.

Removal of Fiber

When the obtained insoluble fraction includes fiber, for example, the above fraction (3) or fractions (1) and (3), as necessary, a soybean emulsion composition in which fiber (okara) is removed and rich taste is more concentrated can be obtained by adding water to the fraction, homogenizing the solution with a high-pressure homogenizer or a Jet Cooker Heater, and then centrifuging the homogenized liquid to recover a supernatant. As necessary, additional step such as heat treatment step and alcohol treatment step can be carried out before or after the homogenization to make protein extraction easier. In this case, fiber content is preferably 10 wt % or less, more preferably 5 wt % or less in terms of dry basis. Fiber content in the present invention can be determined by enzymatic-gravimetric method (Modified Prosky Method) based on "STANDARD TABLES OF FOOD COMPOSITION IN JAPAN Fifth Revised and Enlarged Edition" (Ministry of Education, Culture, Sports, Science and Technology, Japan, 2005).

(Feature and Use of the Soybean Emulsion Composition)

This soybean emulsion composition of the present invention contains a specific range of fat content (neutral lipid and polar lipid) and protein content. Among the protein, especially LP content is high. The soybean emulsion composition optionally contains fiber. In addition, the soybean emulsion composition has concentrated delicious natural taste of soybean, very rich taste and no or little unpleasant taste such as taste of raw vegetation, astringency, and harsh taste. Therefore, the soybean emulsion composition can be used as a raw material for various foods.

Although an emulsion composition similar in composition can be obtained by adding water and fat to conventional soy flour or soybean protein isolate, it is difficult to prepare the composition having similar lipoxygenase protein content and LCI value. The soybean emulsion composition prepared with the above technique has much better taste than the prepared product. Therefore, the soybean emulsion composition has good aptitude for a food raw material.

The fat in this soybean emulsion composition is preferably unrefined soybean oil from the point of taste. That is, most preferable result can be obtained when the fat in this soybean emulsion composition is derived from whole soybean as a raw material. In other words, this soybean emulsion composition prepared from whole soybean in a prescribed method is most preferable as, for example, an action body of the composition for reducing serum cholesterol according to the fifth aspect of the invention.

<Soybean-Derived Raw Material-containing Food or Beverage>

In a broad sense, a soybean-derived raw material-containing food or beverage of the present invention encompasses food in which soybean-derived raw material is used as a milk substitute composition, an acidic soybean material, an egg yolk substitute composition, a raw material for processed soy food or composition for reducing serum cholesterol or improving renal function as described in the following first to fifth aspects of the present invention.

Hereinafter, each of embodiments of the first to fifth aspects of the present invention of which special technical feature is this soybean emulsion composition will be described more specifically.

<Embodiment of the First Aspect of the Invention>

This soybean emulsion composition used in the first aspect of the invention has the above mentioned feature and characteristic rich taste without taste of raw vegetation peculiar to soybean, compared to conventional tofu, soymilk and soybean emulsion composition. Therefore, this soybean emulsion composition can be widely used for a food or beverage in which dairy product such as fresh cream is used, for example, confectionery, bread, dessert, beverage, soup, sauce and the like, beyond the conventional thinking that a soybean-derived food or drink lacks of rich and delicious taste.

In addition, this soybean emulsion composition can be used as a powdered soybean emulsion composition after drying to use as a powdered whole fat milk substitution for the soybean-derived raw material-containing food or beverage of the first aspect of the invention. The first aspect of the invention also encompasses the powdered soybean emulsion composition and the soybean-derived raw material-containing food or beverage using the composition.

The first aspect of the invention relates to a soybean-derived raw material-containing food or beverage containing this soybean emulsion composition as a dairy product substitution. More specifically, the soybean-derived raw material-containing food or beverage of the first aspect of the invention refers to a food or beverage in which a part or all of used dairy product is substituted with this soybean emulsion composition, in raw material for confectionery or bread, confectionery, bread, dessert, beverage, soup, sauce or the like using dairy product such as milk, fresh cream and powdered whole fat milk.

More concretely, the raw material for confectionery or bread refer to oil-in-water emulsion composition such as whipping cream, water-in-oil emulsion composition such as margarine and fat spread, flour paste such as custard, water-containing chocolate such as ganache and fresh cream chocolate cheese-like food with fluid, paste or solid form and the like which are used for any one of topping, coating, sandwich, filling and kneading.

The confectionery and bread refer to entire confectioneries and breads using the above described raw material for confectionery or bread. The dessert refer to jelly, bavarois, pudding, frozen dessert, ice cream and the like in which one or more of the above described raw materials for confectionery or bread is used for any one of topping, coating, sandwich, filling and kneading.

The beverages refer to dairy product such as milk beverage, fermented beverage, fruit juice beverage and coffee creamer in which a part or all of the used dairy product such as milk, fresh cream and powdered whole fat milk is substituted with this soybean emulsion composition.

The soup and sauce refer to entire soups and sauces in which a part or all of the used dairy product such as milk, fresh cream and powdered whole fat milk is substituted with this soybean emulsion composition, and more concretely, refer to soup, stew, gratin, white sauce and the like.

The first aspect of the invention relates to the above described soybean-derived raw material-containing food or beverage with improved taste, that is, an use of this soybean emulsion composition as a dairy product substitution for the raw material for confectionery or bread, confectionery, bread, dessert, beverage, soup, sauce or the like. An additive amount of this soybean emulsion composition is not particularly limited, but about 0.5 wt % or more, preferably 1 to 30 wt %, most preferably 1 to 20 wt % relative to the soybean-derived raw material-containing food or beverage in terms of dry basis. When the amount is less than the lower limit, it is not preferable because taste characteristics of this soybean emulsion composition are not given.

In addition, one or more of sugar, starch, fat, salt, emulsifier, emulsion stabilizer, thickening agent, seasoning, acidulant, spice, coloring agent, antioxidant and the like can be used in combination with this soybean emulsion composition.

The sugar includes maple syrup, honey, unrefined sugar, granulated sugar, maltose, trehalose, maltitol and the like. The starch includes raw starch, hydrogenated starch, modified starch and the like.

The fat include, but not limited to, one or more of vegetable fat such as cocoa butter, rapeseed oil, soybean oil, sunflower seed oil, cottonseed oil, peanut oil, rice bran oil, corn oil, safflower oil, olive oil, sesame oil, palm oil, shea butter, sal fat, coconut oil and palm kernel oil; animal fat such as milk fat, beef tallow, lard and fish oil; single or mixed oil thereof; or modified fat thereof such as hydrogenated, fractionated and interesterified fat.

The emulsifier includes lecithin, sucrose fatty acid ester, glycerol fatty acid ester, polyglycerin fatty acid ester, sorbitan fatty acid ester, diacetal tartaric acid monoglyceride and the like.

The emulsion stabilizer and thickening agent include water-soluble soybean polysaccharide, pullulan, carboxymethylcellulose, agar, gelatin, pectin, carrageenan, guar gum, locust bean gum, sodium alginate and the like.

The spice includes turmeric, mustard, pepper and the like. As a coloring agent, plant color such as carotene and lycopene, and various synthetic colors can be used.

In addition, as an antioxidant, tocopherol, catechin, flavon such as rutin, ascorbic acid derivative, plant extract such as rosemary extract and arbutus extract can be used.

In addition, the first aspect of the invention relates to a process for improving a taste of soybean-derived raw material-containing food or beverage such as confectionery, bread, dessert, beverage, soup and sauce. By using this soybean emulsion composition which has significantly improved taste compared to conventional soybean-derived material, taste of confectionery, bread, dessert, beverage, soup, sauce or the like can be significantly improved. In addition, substitution of this soybean emulsion composition for a part or all of dairy product such as milk, fresh cream and powdered whole fat milk, enable to obtain a food or beverage having excellent taste.

Moreover, the first aspect of the invention relates to a process for producing a soybean-derived raw material-containing food or beverage having significantly improved taste in the production of the soybean-derived raw material-containing food or beverage such as confectionery, bread, dessert, beverage, soup and sauce. A soybean-derived raw material-containing food or beverage having rich taste derived from soybean without taste of raw vegetation can be easily obtained by substituting this soybean emulsion composition for a part or all of dairy product such as milk, fresh cream and powdered whole fat milk.

<Embodiment of the Second Aspect of the Invention>
(Acidic Soybean Material)

An acidic soybean material obtained by acidification of a material comprising this soybean emulsion composition with a lactic acid fermentation or an addition of acid and a process for producing same will be explained.

Raw Material

A raw material of the acidic soybean material of the second aspect of the invention includes this soybean emulsion composition. An acidic soybean material having little unpleasant taste such as degradation smell, acetic acid smell and astringency which is generated in a lactic fermentation of conventional soymilk or soybean protein isolate can be obtained by using this soybean emulsion composition. A content of this soybean emulsion composition in the raw material can be 30 to 100 wt %, preferably 60 to 100 wt %, more preferably 90 to 100 wt %.

A protein content in the raw material in terms of dry basis is preferably 7 wt % or more, preferably 15 wt % or more, more preferably 20 wt % or more, and preferably 50 wt % or less.

A fat content in the raw material in terms of dry basis is preferably 10 wt % or more, preferably 20 wt % or more, more preferably 30 wt % or more, and preferably 75 wt % or less. In addition, fat content relative to protein content is preferably 100 wt % or more, more preferably 120 to 250 wt %, further preferably 120 to 200 wt %.

LCI value of the soybean protein included in the raw material may vary according to addition of auxiliary raw material, but is preferably 55% or more, preferably 58% or more, more preferably 60% or more, further preferably 63% or more, most preferably 65% or more.

Water content of the raw material affects a hardness of the obtained acidic soybean material, and can be adjusted according to intended quality, for example, 40 to 95 wt %.

A raw material and additive such as sugar, fat, starch, protein, pH adjuster, polysaccharide thickener, gelling agent, emulsifier, flavor, acidulant, antioxidant and chelating agent can be added in addition to this soybean emulsion composition.

In the case of lactic acid fermentation, if necessary, assimilable sugar can be added as a nutrient source of lactic acid bacterium. For example, glucose, fructose, sucrose, maltose, galactose, lactose, raffinose, trehalose, soybean oligosaccharide, fructo-oligosaccharide, xylo oligosaccharide and the like can be used. These sugar materials can be used alone or in combination of two or more kinds. An adding amount of the assimilable sugar relative to a dry matter of this soybean emulsion composition is preferably 0 to 50 wt %, preferably 0 to 20 wt %.

As for a fat content of an acidic soybean material of the second aspect of the invention, fat content derived from this soybean emulsion composition allows to provide enough rich taste. In addition, additional fat can be separately added for enhancing rich taste by increasing fat and for adjusting a hardness of body of the acidic soybean material. As a result, the fat content in the acidic soybean material can be adjusted to as many as 3 to 40 wt %.

As the additional fat, one or two or more fats selected from animal fat or vegetable fat, or processed fat such as hydrogenated fat thereof, fractionated fat thereof, interesterified fat thereof, diglyceride and medium chain fatty acid-containing fat can be used. Examples of the animal fat and vegetable fat include soybean oil, rapeseed oil, rice oil, sunflower seed oil, safflower oil, palm oil, palm kernel oil, coconut oil, corn oil, cottonseed oil, peanut oil, sal fat, shea butter, beef tallow, milk fat, lard, cacao butter, fish oil, whale oil, mustard oil and the like. Vegetable fat is preferably used. Especially, fractionated palm oil, hydrogenated rapeseed oil and the like are preferably from a viewpoint of adding a texture with smooth melting in the mouth. Melting point of fat can be properly selected in consideration of a hardness of the product, but is preferably 5 to 40° C.

If necessary, raw material of the acidic soybean material of the second aspect of the invention can be homogenized by a suitable homogenizing means such as homogenizer, for example, when additional fat is separately added. In this case, a skilled person in the art can adjust a homogenization pressure according to an intended quality because the pressure affects a hardness of texture of the no-baked cheese cake-like food. In general, the pressure is preferably 2.5 to 15 MPa (25 to 150 kg/cm$^2$).

Acidification

Next, the above raw material is acidified. That is, pH of the raw material is adjusted to acidic. As means for acidification, a method of adding acid, a method of lactic acid fermentation and a combination thereof can be used. In general, pH of 3.5 to 6.0, preferably 4 to 5.9, more preferably 5.0 to 5.8 is preferable. In the case of addition of acid, similar pH range can also be adopted. When pH is too low, acidic taste is too strong and coarse texture tends to occur. When pH is too high, sour taste due to acidification is too weak, in particular, fermented taste is poor in the case of lactic acid fermentation.

In the case of adjusting pH acidic by adding acid, acid to be used is not particularly limited, but includes inorganic acid such as phosphoric acid, hydrochloric acid and sulfuric acid, and organic acid such as citric acid, malic acids, lactic acid, gluconic acid and GDL. One acid alone or combination of two or more acids from these acids can be used. Organic acid is preferably used from a viewpoint of taste.

In the case of adjusting pH acidic by lactic acid fermentation, lactic acid bacterium to be used is not particularly limited and lactic acid bacterium which is generally used for fermented milk product such as yogurt, lactic acid bacteria beverage and cheese can be used. For example, genus *Lactobacillus* such as *Lactobacillus casei*, *Lactobacillus plantarum*, *Lactobacillus helveticus*, *Lactobacillus bulgaricus*, *Lactobacillus gasseri*, *Lactobacillus acidophilus*, *Lactobacillus lactis*, *Lactobacillus salivarius* subsp. *salivarius*, *Lactobacillus gallinarum*, *Lactobacillus amylovorus*, *Lactobacillus brevis* subsp. *brevis*, *Lactobacillus fermentum*, *Lactobacillus mali*, *Lactobacillus delbrueckii*, *Lactobacillus johnsonii*, *Lactobacillus sanfranciscensis*, *Lactobacillus panex*, *Lactobacillus comoensis*, *Lactobacillus italicus*, *Lactobacillus leichmannii*, *Lactobacillus curvatus*, *Lactobacillus hilgardii*, *Lactobacillus reuteri*, *Lactobacillus pastorianus*, *Lactobacillus buchneri*, *Lactobacillus cellobiosus*, *Lactobacillus fructivorans* and *Lactobacillus lactis* subsp. *cremoris*; genus *Streptococcus* such as *Streptococcus thermophilus*, *Streptococcus lactis* and *Streptococcus diacetylactis*; genus *Lactococcus* such as *Lactococcus lactis* subsp. *lactis*, *Lactococcus lactis* subsp. *cremoris*, *Lactococcus lactis* subsp. *diacetylactis* and *Lactococcus lactis* subsp. *lactis* biovar *diacetylactis*; and genus *Leuconostoc* such as *Leuconostoc mesenteroides* subsp. *cremoris*, *Leuconostoc lactis* and *Leuconostoc pseudomesenteroides* can be used. In addition, a starter in which microorganism other than lactic acid bacterium, for example, yeast such as kefir yeast, is mixed can also be used.

In the second aspect of the invention, genus *Bifidobacterium* is also included in the lactic acid bacterium. For example, *Bifidobacterium bifidum*, *Bifidobacterium longum*, *Bifidobacterium infantis*, *Bifidobacterium breve*, *Bifidobacterium adolescentis*, *Bifidobacterium angulatum*, *Bifidobacterium catenulatum*, *Bifidobacterium pseudocatenulatum*, *Bifidobacterium dentium*, *Bifidobacterium globosum*, *Bifidobacterium pseudolongum*, *Bifidobacterium cuniculi*, *Bifidobacterium choerinum*, *Bifidobacterium animalis*, *Bifidobacterium thermophilum*, *Bifidobacterium bourn*, *Bifidobacterium magnum*, *Bifidobacterium asteroides*, *Bifidobacterium indicum*, *Bifidobacterium gallicum*, *Bifidobacterium lactis*, *Bifidobacterium inopinatum*, *Bifidobacterium denticolens*, *Bifidobacterium pullorum*, *Bifidobacterium suis*, *Bifidobacterium gallinarum*, *Bifidobacterium ruminantium*, *Bifidobacterium merycicum*, *Bifidobacterium saeculare*, *Bifidobacterium minimum*, *Bifidobacterium subtile*, *Bifidobacterium coryneforme* and the like can be used. In addition, these lactic acid bacteria can be used alone or in any combination of two or more of bacteria.

An additive amount of the lactic acid bacterium can be adjusted according to fermentation temperature, fermentation time. Fermentation condition is preferably at 10 to 50° C. for 3 to 48 hours, preferably at 15 to 45° C. for 4 to 30 hours. A pH after the fermentation can be properly fine-adjusted by using alkali or acid according to a preference.

Separation of Whey

If necessary, the acidified product adjusted to a suitable pH can be subjected to a process of separating whey by a centrifuge or the like and recovering curd. In the case of separating whey, a whey separated type cheese-like acidic soybean material which is solid or semi-solid form having high solid content and moderate hardness can be produced. In addition, taste can be adjusted to a little acidity by separating whey.

On the other hand, in the case of not separating whey, a whey non-separated type cheese-like acidic soybean material which is liquid or paste form having low solid content can be produced. A skilled person in the art can properly decide whether whey is separated in consideration of a physical property that is appropriate for the usage of a food to be produced.

Additive

Next, after the above acidification of raw material, if necessary, salt such as chloride such as sodium chloride and potassium chloride and phosphate such as sodium polyphosphate can be added to the acidified product before separating whey or the curd obtained by removing whey from the acidified product. These additives can be added before the acidification treatment.

Especially, it is preferable to add polymer phosphate such as sodium polyphosphate because acidic taste can be reduced and rich taste can be further enhanced, coarse texture can be reduced and smooth texture can be increased by adding phosphate. The additive amount of phosphate is not particularly limited, but preferably 0.5 to 15 wt % relative to protein in the acidic soybean material. When amount of phosphate is too low, the effect of reducing coarse texture is reduced. When amount of phosphate is too high, astringency tends to be strong.

Next, if necessary, the acidified product or the curd is heat pasteurized. The heat condition is not particularly limited, but is preferably at 70 to 85° C. for 1 second to 15 minutes. If necessary, homogenization with a homogenizer or the like is carried out after the heat pasteurization, and then cooling to about 4 to 10° C. to obtain the acidic soybean material.

Cheese Type and Yogurt Type

An acidic soybean material of the second aspect of the invention can be cheese type material or yogurt type material by varying kinds of raw material, kinds of lactic acid bacterium and fermentation condition (temperature, time and the like).

The cheese type material is a material obtained by a process similar to an existing process for producing cheese, or a material having similar property (such as hardness and taste) to an existing cheese by adding an auxiliary material such as starch and fat. It is divided roughly into natural cheese and process cheese as a kind of an existing cheese. A typical embodiment of the second aspect of the invention includes unripened type such as fresh cheese and cream cheese. More specifically, fresh cheese includes cottage cheese, fromage bran, mozzarella cheese, ricotta cheese, mascarpone, casu marzu, feta cheese, panīr, rŭshàn and the like. In addition, it is also possible to make the material ripened cheese such as washed rind cheese, white-rind cheese, blue vein cheese, semi-hard cheese and hard cheese, other than fresh cheese. Typical examples of the ripened cheese include gouda cheese, edam cheese, camembert cheese, cheddar cheese and the like.

The yogurt type material is a material obtained by a process similar to an existing process for producing yogurt, or a material having similar property (such as physical property and taste) to an existing yogurt by adding an auxiliary material. An existing yogurt includes yogurt prepared in all over the world such as Bulgarian yogurt and Russian kefir yogurt other than Japanese.

(Usage to Food of the Acidic Soybean Material)

An acidic soybean material of the second aspect of the invention has a combination of good rich taste of soybean and rich taste generated by acidification (especially, lactic acid fermentation), and thereby, has rich taste similar to fermented milk product, refreshing aftertaste and smooth texture. Therefore, the acidic soybean material can be used as a part or all of substitution for fermented milk product such as cheese and yogurt in the same usage (i.e. as a fermented milk substitution). The acidic soybean material can be used in various foods as a main raw material as a base of formulation or an auxiliary raw material for kneading, filling, topping or nappe. A main raw material is a raw material which is base of food formulation, and is included about 20 wt % or more in the food, but it is not limited to this amount. In addition, the auxiliary raw material means a raw material which is mixed, injected, adhered or spread to a main raw material which is a base of the formulation.

For example, this acidic soybean material as is can be provided as a product for eating. In addition, material for processed food such as flour paste, filling and sour cream can be prepared by adding other raw material to the acidic soybean material. Further, the acidic soybean material can be widely used as a raw material for sauce such as cream sauce and curry sauce, and can be used with directly adding as a raw material for confectionery or bread. Moreover, the acidic soybean material can be used as filling or topping for marine products such as chikuwa (a tube-shaped fish paste cake) and processed meat products such as hamburger.

In the field of confectionery, this acidic soybean material has a taste suitable for both western confectionery and Japanese-style confectionery, especially suitable for unbaked confectionery in the western confectionery and Japanese-style confectionery. Examples of the western confectionery include cheese cake, tart, sponge cake, pound cake, Castella (A type of sponge cake in Japan), baumkuchen, cream puff, waffle, cookie, pie, souffle, tiramisu, pudding, bavarois and the like. Examples of the Japanese-style confectionery include rice cakes, rice dumplings, Youkan (adzuki-bean jelly), Uiro (sweet rice jelly), Dora-yaki (bean jam pancake), Tai-yaki (fish-shaped bean jam pancake) and the like.

Hereinafter, examples of unbaked western confectionery will be described as more specific aspects of confectionery.

No-bake Cheesecake-like Food

A no-bake cheesecake-like food can be produced by using the whey non-separated type acidic soybean material as a main raw material in substitution for filled type cheese material (for example, "Fromage Bran Assortie" manufactured by Fuji Oil Co., Ltd.).

It is preferable to add this acidic soybean material in the food at a content of 5 to 70 wt %, preferably 20 to 60 wt %. As another raw material, a raw material which is generally used for no-bake cheese cake, for example, milk raw material such as milk and cream, sugar such as liquid sugar and granulated sugar, egg white used for meringue, gelling agent such as gelatin and the like can be used. In addition, if vegan food is desired, soymilk, soy flour, soybean protein isolate, soybean cream prepared from these soybean materials and the like can be used in substitution for the milk raw material. The obtained no-bake cheesecake-like food has a quality comparable to a no-bake cheesecake made from cheese or filled type cheese. In addition, the food has rich taste and freshness and smooth texture derived from soybean.

Baked Cheesecake-like Food

A baked cheesecake-like food can be produced by using the whey separated type acidic soybean material as a main raw material in substitution for filled type cheese material (for example, "Créme Fromage" manufactured by Fuji Oil Co., Ltd.).

It is preferable to add this acidic soybean material in the food at a content of 5 to 70 wt %, preferably 20 to 60 wt %. As another raw material, a raw material which is generally used for baked cheese cake, for example, milk raw material such as cream, sugar such as granulated sugar, white chocolate, eggs such as whole egg and egg yolk, starch such as corn starch and the like can be used.

The obtained baked cheesecake-like food has an appearance comparable to baked cheesecake made from cheese or filled type cheese and a rich taste. In addition, texture thereof is floury sweet potato-like texture different from conventional baked cheesecake, and thus, novel baked cheesecake-like food different from conventional baked cheesecake can be obtained.

<Embodiment of the Third Aspect of the Invention>
(Egg Yolk Substitute Composition)

An egg yolk substitute composition of the third aspect of the invention includes this soybean emulsion composition, and can substitute for a part or all of egg yolk in various foods. The egg yolk in various foods that can be substituted in the third aspect includes raw egg yolk, pasteurized egg yolk, salted egg yolk, sweetened egg yolk, dried egg yolk and the like.

The egg yolk substitute composition of the third aspect can be used as an egg yolk substitution with improved quality and physical property by adding sugar, starch, spice, antioxidant, fat, coagulant agent and the like to this soybean emulsion composition. These ingredients can be used in combination with one or more ingredients.

In addition, the egg yolk substitution of the third aspect can be used as an egg yolk substitution with improved quality and physical property by acting protein cross-linking enzyme to this soybean emulsion composition or by acting protein cross-linking enzyme to a mixture prepared by adding one or more material from a group consisting of sugar, starch, spice, fat, antioxidant and coagulant agent to this soybean emulsion composition.

Sugar

The egg yolk substitute composition of the third aspect can be prepared as an egg yolk substitution having further improved taste by adding sugar to this soybean emulsion composition. Sugar disclosed herein includes disaccharide to oligosaccharide, more specifically, maple syrup, honey, unrefined sugar, granulated sugar, table sugar, caramel, fructose, high fructose cone syrup, starch syrup, maltose, maltotriose, trehalose, maltitol and the like. These sugars can be used in combination of one or more kinds.

A content of the above sugar in the egg yolk substitution is preferably 0.5 to 50 wt %, more preferably 3 to 30 wt %.

Spice

The egg yolk substitute composition of the third aspect can be prepared as an egg yolk substitution having further improved taste by adding spice to this soybean emulsion composition. Spice includes mustard, wasabi (green horseradish paste), thyme, basil, anise seed, clove, fennel, ginger, cinnamon, pepper, turmeric, paprika, fenugreek seed, nutmeg, star anise, oregano, laurel, marjoram, rosemary, peppermint, tarragon, dill seed and the like. These spices can be used in combination of one or more kinds.

A content of the above spice in the egg yolk substitution is preferably 0.001 to 20 wt %, more preferably 0.01 to 10 wt %.

Antioxidant

The egg yolk substitute composition of the third aspect can be prepared as an egg yolk substitution having suppressed taste degradation due to oxidation by adding antioxidant to this soybean emulsion composition. Antioxidant includes tocopherol, arbutus extract, ascorbic acid, catechin, tea extract, material having chelating effect such as sodium citrate and the like. These antioxidants can be used in combination of one or more kinds.

A content of the above antioxidant in the egg yolk substitution is preferably 0.001 to 20 wt %, more preferably 0.01 to 10 wt %.

Fat

The egg yolk substitute composition of the third aspect can be prepared as an egg yolk substitution given an effect of improving physical property such as rich body by adding fat to this soybean emulsion composition. Fat can be used as long as the fat is edible, and includes soybean oil, rapeseed oil, corn oil, cottonseed oil, olive oil, peanut oil, rice oil, safflower oil, sunflower seed oil, palm oil, palm kernel oil, coconut oil, sal fat, mango butter, milk fat and the like, and physically or chemically processed fat thereof such as hydrogenated fat, fractionated fat and interesterified fat thereof. These fats can be used in combination of one or more kinds.

A content of the above fat in the egg yolk substitution is preferably 0.5 to 50 wt %, more preferably 3 to 30 wt %.

Starch

The egg yolk substitute composition of the third aspect can be prepared as an egg yolk substitution given an effect of improving physical property such as rich body by adding starch to this soybean emulsion composition. Available starch includes corn starch, waxy corn starch, wheat starch, rice starch, potato starch, tapioca starch, sweet potato starch, sago starch and the like, and modified starch thereof. The available modified starch includes, for example, oxidized starch, acid treated starch, enzyme-treated starch, starch acetate, starch phosphate, starch succinate, starch octenylsuccinate, hydroxypropyl starch, cross-linked starch, moist heat-treated starch and the like. These starches can be used in combination of one or more kinds.

A content of the above starch in the egg yolk substitution is preferably 0.5 to 50 wt %, more preferably 3 to 30 wt %.

Coagulant Agent

The egg yolk substitute composition of the third aspect can be prepared as an egg yolk substitution given a function of coagulation similar to egg yolk by adding coagulant agent to this soybean emulsion composition. Coagulant agent includes brine, calcium chloride, magnesium chloride, glucono-delta-lactone, calcium sulfate and the like. These coagulant agents can be used in combination of one or more kinds.

A content of the above coagulant agent in the egg yolk substitution is preferably 0.001 to 10 wt %, more preferably 0.01 to 5 wt %.

Protein Cross-linking Enzyme

The egg yolk substitute composition of the third aspect can be prepared as an egg yolk having improved emulsifying property such as emulsifying capacity by acting protein cross-linking enzyme to this soybean emulsion composition. This high emulsifying property provides superior performance in the case of preparing emulsion under acidic condition.

The protein cross-linking enzyme is not limited as long as the enzyme catalyzes cross-linking of protein molecules, but includes an enzyme which catalyzes a condensation reaction between glutamine residue and lysine residue involving amino group and a reaction involving ε-amino group such as condensation reaction between asparagine residue and lysine residue. In addition, an enzyme which catalyzes a condensation reaction between thiol groups in cysteine residue without involving amino group can also be used. More specifically, the enzyme includes transglutaminase which catalyzes a condensation between glutamine residue and lysine residue and thiol-disulfide exchange enzyme which catalyzes a condensation between two thiol groups and a formation of disulfide bond, and the like. These enzymes can be used in combination of one or more kinds.

Among these enzymes, it is preferable to use transglutaminase. Origin of transglutaminase is not particularly limited, and any of animal-origin, microorganism-origin and plant-origin can be used. In addition, any of purified enzyme and commercially available preparation can be used.

A used amount of the protein cross-linking enzyme relative to a content of this soybean emulsion composition in terms of dry basis is preferably 0.1 wt % or more, more preferably 0.5 wt % or more, further preferably 0.9 wt % or more. In addition, the amount of enzyme is preferably 15 wt % or less, more preferably 10 wt % or less because the effect may not be increased when the amount is too high.

It is preferable that a reaction temperature of the protein cross-linking enzyme is about 10 to 80° C, preferably 20 to 70° C., more preferably 40 to 60° C. When the temperature is too low, reaction speed may be slow. When the temperature is too high, enzyme deactivation may be promoted.

It is preferable that a reaction time of the protein cross-linking enzyme is about 0.01 to 120 minutes, preferably 1 to 60 minutes. When the reaction time is too short, enough reaction effect may not be obtained. Even if the reaction time is too long, it does not make a difference in the effect.

Other Raw Materials

If necessary, the egg yolk substitute composition of the third aspect can be used with adding emulsifier, thickening agent, gelling agent, protein, inorganic salt, organic salt, coloring agent, flavor, acidulant and the like.

(Egg Yolk Substitute Food)

An egg yolk substitute composition including this soybean emulsion composition can be used to various foods described in later. An egg yolk substitute food having rich taste and suppressed taste of raw vegetation derived from soybean can be obtained by adding the egg yolk substitute composition including this soybean emulsion composition.

An additive amount of the egg yolk substitute composition including this soybean emulsion composition is not particularly limited as long as a taste characteristic of this soybean emulsion composition is clearly appeared, but about 0.5 wt % or more, preferably 0.5 to 60 wt %, most preferably 1 to 50 wt % relative to the egg yolk substitute food in terms of dry basis. When the amount is less than lower limit, it is not preferable because a taste characteristic of this soybean emulsion composition is not clearly appeared. The egg yolk substitute food of the third aspect of the invention can be produced by a general production process for producing each food. In addition, the egg yolk substitute food of the third aspect of the invention can be produced by adding the above mentioned sugar, starch, spice, antioxidant, fat, coagulant agent, emulsifier, thickening agent, gelling agent, protein, inorganic salt, organic salt, coloring agent, flavor, acidulant and the like as well as the egg yolk substitute composition, and by acting protein cross-linking enzyme to the egg yolk substitute composition.

The egg yolk substitute food of the third aspect of the invention includes seasoning, confectionery, sauce and daily dish.

Seasoning

A seasoning in the present invention includes dressing, baste or sauce, mayonnaise, dried seasoning and the like.

The dressing includes semisolid dressing, emulsified liquid dressing, separate liquid dressing and the like.

The baste or sauce, which is a flavored liquid for simmered food or grilled food, includes sauce for barbecued meat, baste for grilled chicken, dipping sauce for shabushabu (thin slices of beef parboiled in hot soup), sauce for boiled meat or boiled seafood and the like.

The mayonnaise includes mayonnaise, mayonnaise-style flavored liquid, mayonnaise-like flavored liquid and the like.

As for the mayonnaise, mayonnaise maintaining good emulsion state and having good taste can be prepared by using the egg yolk substitute composition obtained by acting protein cross-linking enzyme even if 100% of egg yolk is substituted in a system including 70 wt % or more of fat.

Confectionery

A confectionery in the present invention includes, for example, cream, dessert, baked confectionery and the like.

The cream, which is prepared by mixing and emulsifying oil phase and aqueous phase, includes, for example, custard, ice cream, whipped cream and the like. As for the custard, custard-like food can be prepared by mixing the egg yolk substitute composition of the third aspect of the present invention and white chocolate. The white chocolate used in the third aspect of the present invention includes a white chocolate for coating. Chocolate used herein refers to chocolate, semi-chocolate or chocolate food, which is defined by Japan Chocolate Fair Trade Council and Japan Chocolate Food Fair Trade Council.

In the third aspect of the present invention, blending ratio of white chocolate to the egg yolk substitute composition is not particularly limited, but about 1:99 to 99:1 (weight ratio). It can be prepared with varying the weight ratio depending on a physical property of the white chocolate such as melting point.

The dessert includes pudding, bavarois, brulee and the like. The pudding includes custard pudding and the like. The custard pudding includes a baked pudding prepared by baking in an oven and a steamed pudding prepared by steam-heating in a retort oven, a steamer or the like.

The baked confectionery includes sponge cake, pound cake, tube cake, pancake, Swiss roll, Castella, doughnut, madeleine, biscuit, cookie, brioche, muffin, waffle, brownie, souffle and the like.

Sauce

A sauce in the present invention includes carbonara sauce, cream sauce, cream soup, Sauce Hollandaise, custard sauce, tartare sauce and the like. As above illustrated, soup is also included in the sauce.

Daily Dish

A daily dish of the present invention includes chawan-mushi (steamed egg hotchpotch), tamago-tofu (steamed egg custard), tamago-zosui (rice porridge with egg) and the like.

<Embodiment of the Fourth Aspect of the Invention >

(Processed Soy Food)

A processed soy food of the fourth aspect of the invention includes this soybean emulsion composition as a raw material. Preferably, the processed soy food is prepared by using soybean raw material such as soymilk and powdered soybean protein and substituting a part or all of the soybean raw material with this soybean emulsion composition. More specifically, the processed soy food includes tofu, yuba, soybean seasoning, abura-age, ganmodoki, atsu-age, soymilk beverage and the like, and a food similar to them.

This soybean emulsion composition formulated in the processed soy food can be formulated as a substitute for a part or all of soybean material such as soymilk and powdered soybean protein, which is a general raw material, and thereby, texture and taste of the processed soy food can be improved. A substitution ratio depends on a kind of processed soy food, but can be 10 wt % or more, preferably 15 wt % or more, more preferably 20 wt % or more of soybean raw material such as soymilk. In addition, it is also possible to 25 wt % or more. Further, it is also possible to 50 wt % or more, 70 wt % or more, 90 wt % or more, or 100 wt % depending on a desired quality. Hereinafter, aspects of the specific processed soy food will be explained, but a kind of the processed soy food is not limited to the following aspects.

Tofu

Tofu can be produced by mixing a coagulant agent with this soybean emulsion composition or a mixture of this soybean emulsion composition and soymilk, and then heating to coagulate protein. Tofu can be produced by well known process without difficulty. Coagulant agent includes brine (magnesium chloride), calcium chloride, calcium sulfate, GDL and the like. An adding amount of the coagulant agent is not particularly limited, for example, can be 0.1 to 5 wt %, preferably 0.3 to 3 wt % relative to this soybean emulsion composition and soymilk in terms of dry basis. A hardness of tofu can be properly adjusted by increasing or decreasing an amount of the coagulant agent. If high hardness is desired, the amount of the coagulant agent can be increased. If tofu having softer and creamy texture is desired, coagulant agent can be added at a little amount. Thus, the obtained tofu will have soft and creamier texture than conventional tofu and good texture melting in the mouth and rich taste without grassy soybean smell.

In addition, various additives used in conventional process for production of tofu can be added. For example, salt, oligosaccharide, polysaccharide, starch, protein and the like can be added alone or in combination other than coagulant agent.

Yuba

Yuba can be produced by heating or freezing this soybean emulsion composition alone or in combination with soymilk as a raw material to form membranal denaturated material on the surface, and then recovering the material. A process for producing yuba can be carried out with well known means.

The obtained yuba has a smooth texture similar to fresh yuba (fresh lifted-up yuba) and richer taste than conventional yuba. In addition, for modifying the texture, yuba can be prepared by adding salt, polysaccharide, starch, protein and the like alone or in combination to this soybean emulsion composition.

Soybean Seasoning

A soybean seasoning can be produced by adding this soybean emulsion composition to a raw material of seasoning. The seasoning includes ponzu (vinegar and acidic citrus juice), soy sauce, mayonnaise, dressing, sauce, ketchup, baste, soup stock, and liquid or powdered seasoning attached to product such as instant noodle.

This soybean emulsion composition can be formulated in the seasoning at a content of, for example, 20 to 80 wt %.

Abura-age, Ganmodoki, Atsu-age

A processed soy food such as abura-age, ganmodoki and atsu-age can be prepared by using this soybean emulsion composition as a part of raw material with a well known production process. As a raw material dough of these processed soy foods, both tofu with conventional production process and soybean protein paste obtained by kneading powdered soybean protein, water and fat with a cutting machine followed by emulsifying, can be used.

When atsu-age is prepared by using this soybean emulsion composition, a texture and taste similar to tofu which is prepared by using this soybean emulsion composition can be added.

In addition, when this soybean emulsion composition is used to abura-age and ganmodoki, not only rich soybean taste can be added, but also expansion of dough material in a cooking of deep-frying is more improved, and thereby an effect of improving an expansion rate can be obtained. Moreover, absorbing amount of flavored liquid is improved and more juicy texture can be obtained by improving the expansion rate.

Soymilk Beverage

A soymilk beverage is not a soymilk for producing tofu product, but a beverage prepared by using soymilk that is drunk by general consumer during recent years. The soymilk beverage of the fourth aspect of the invention includes all beverages in which soymilk is used regardless of the product standard. Rich taste of soybean and creamy texture can be added when this soybean emulsion composition is used for the soymilk beverage.

Frozen Processed Soy Food

A processed soy food of the fourth aspect of the invention can be a processed soy food having freezing resistance which maintains a texture before freezing even after freezing and unfreezing by adding well known anti-freeze denaturation agent such as oligosaccharide, polysaccharide, starch and gelatin. These can be commercially available frozen product such as frozen tofu, frozen yuba, frozen atsu-age, frozen ganmodoki and frozen abura-age. An additive amount of the anti-freeze denaturation agent is preferably 0.1 to 10 wt % in the tofu or the like.

For example, conventional frozen tofu has plain and poor soybean taste and hard texture with remaining in the mouth. However, according to the fourth aspect of the invention, similar effect in the case of using this soybean emulsion composition to tofu can be obtained in the case of frozen tofu.

Dried Processed Soy Food

A processed soy food of the fourth aspect of the invention can be dried processed soy food such as dried tofu, dried yuba, dried soybean seasoning, dried abura-age and powdered soymilk by various means such as freeze drying, spray drying, microwave drying, oven drying, natural drying and drying under reduced pressure.

When the processed soy food of the fourth aspect of the invention is abura-age, the abura-age can be used as an ingredient for table-ready food by carrying out drying after cooking such as immersing abura-age after deep-frying to flavored liquid including various seasonings. Because the abura-age of the fourth aspect of the invention has good expansion property by using this soybean emulsion composition, the abura-age maintains its volume after cooking and drying, and has volume and good reconstruction property (reconstruction by hot water) in the case of reconstituting by pouring hot water.

<Embodiment of the Fifth Aspect of the Invention>

The present inventors have found that this soybean emulsion composition has strong effect of reducing serum cholesterol and improving renal function. The effect of reducing serum cholesterol and improving renal function can be observed by eating an appropriate amount of this soybean emulsion composition. That is, this soybean emulsion composition can be used as an action body of composition for reducing serum cholesterol or composition for improving renal function.

A content of this soybean emulsion composition in the composition for reducing serum cholesterol or composition for improving renal function of the fifth aspect of the invention is 1 to 100 wt %, preferably 50 to 100 wt %, more preferably 80 to 100 wt %, most preferably 100 wt %.

In addition, a food having an effect of reducing serum cholesterol or improving renal function can be produced by adding an appropriate amount of the composition for reducing serum cholesterol or composition for improving renal function of the fifth aspect of the invention to food. Preparing a "food having an effect of reducing serum cholesterol" or "food having an effect of improving renal function" without difficulty can be introduced for the first time by that the composition for reducing serum cholesterol of the fifth aspect of the invention has both good taste and an effect of reducing serum cholesterol. That is, it is achieved by the fifth aspect of the invention for the first time. Further, a food for specified health use or a food for special dietary uses (food for sick person, food for person with dysphagia) having an effect of reducing serum cholesterol or improving renal function can be prepared by using the composition for reducing serum cholesterol or composition for improving renal function of the fifth aspect of the invention.

The process for producing the food having an effect of reducing serum cholesterol or improving renal function has a technical feature that a "composition for reducing serum cholesterol" or "composition for improving renal function" of the fifth aspect of the invention is included in food.

The above described embodiments of first to fifth aspects of the invention has common specific technical feature that the above described specific novel soybean emulsion composition is used. It goes without saying that it is possible to be an aspect fusing any two or more of ideas from each technical idea. That is, this soybean emulsion composition can function as, for example, both milk substitute composition and egg yolk substitute composition, both milk substitute composition and composition for reducing serum cholesterol or composition for improving renal function, and both egg yolk substitute composition and composition for reducing serum cholesterol or composition for improving renal function in a food to be used.

EXAMPLES

Examples of the present invention will be described below. The "%", "parts" described below refers to "wt %", "parts by weight" unless otherwise specified. Measurement of fat is carried out based on the chloroform/methanol mixed solvent extraction method unless otherwise noted.

Production Example 1

Preparation of a Soybean Emulsion Composition 1

To 3.5 kg of soy flour which was subjected to wet heat treatment to make NSI of 59.4 was added with 4.5 times its weight of water at 50° C. to prepare suspension liquid. The suspension liquid was stirred for 30 minutes with keeping warm for water extraction. The pH of the suspension liquid at this time was 6.7. Centrifugation with three phase separation system was continuously carried out at 6,000×g to separate to (1) floating layer, (2) mid layer and (3) precipitate layer. Then, 6.3 kg of soybean emulsion composition as combination of the floating layer and the precipitate layer was recovered to prepare a soybean emulsion composition A.

Production Example 2

Preparation of a Soybean Emulsion Composition 2

To the soybean emulsion composition A obtained in Production Example 1 was added with 0.5 times its weight of water. The mixture was homogenized with high pressure homogenizer at 13 MPa. The homogenized liquid was heated with direct steam blowing heating at 142° C. for 7 seconds. The liquid was subjected to continuous centrifugation at 6,000×g to separate and remove insoluble fiber. The supernatant fraction was recovered to prepare a soybean emulsion composition B.

A part of the soybean emulsion compositions A and B obtained from Production Examples 1 and 2 were lyophilized for analysis. And, as general constituent, dry matter, and protein (by Kjeldahl method), fat (by chloroform/methanol mixed solvent extraction method) and ash in terms of dry basis were measured. In addition, LCI value as estimated value of lipoxygenase protein content and LP content was analyzed by SDS-PAGE. For comparison, soy flour used as a raw material and commercially available soybean emulsion composition "Soy Supreme Kreme" (manufactured by SunOpta Grains and Foods Group, powder form), which is believed to be produced by a method described in U.S. Pat. No. 6,548,102, were measured in the same manner. Each analytical value is shown in table 2.

TABLE 2

| | Dry matter (%) | In terms of dry basis (%) | | | Protein composition (%) | |
|---|---|---|---|---|---|---|
| | | Protein | Fat | Ash | Lipoxygenase | LCI |
| Soy flour | 95.3 | 43.1 | 30.0 (69.6)* | 5.0 | 3.6 | 57 |
| Soybean emulsion composition A | 30.6 | 32.2 | 43.0 (134) | 4.3 | 6.2 | 67 |
| Soybean emulsion composition B | 18.2 | 32.2 | 58.9 (183) | 3.9 | 6.1 | 67 |
| Commercially available Soybean emulsion composition "Soy Supreme Kreme" | 97.0 | 32.0 | 54.5 (170) | 4.5 | 2.0 | 50 |

*Fat contents (%) relative to protein content are in parentheses.

The soybean emulsion compositions A and B were rich in fat content relative to protein compared to soy flour. In addition, they had different protein composition from soy flour and commercially available soybean emulsion composition. That is, LP was concentrated and lipoxygenase protein content was high because LCI value was high value, 60 or more. The soybean emulsion composition having such a composition has novel ingredient composition of which conventional soymilk and okara does not have.

The compositions A and B had significantly rich taste in which natural delicious taste derived from known soymilk or soybean was concentrated without taste of raw vegetation, astringent taste and harsh taste. On the other hand, the commercially available soybean emulsion composition had poor rich taste and strong taste of raw vegetation and astringent taste due to lower LCI value than that of soy flour and lower lipoxygenase protein content, compared to the compositions A and B.

Specific Examples of the First Aspect of the Invention

Example a1

Preparation of Whipped Cream

A mixture of 29.9% of the soybean emulsion composition B prepared in the Production Example 2, 29.9% of hydrogenated palm kernel oil (melting point: 34° C.), 1.4% of high fructose corn syrup (FC: manufactured by Oji Cornstarch Co., Ltd.), 1.4% of oligotose (manufactured by Mitsubishi-Kagaku Foods Corporation), 37.0% of water, 0.2% of lecithin, 0.1% of sucrose fatty acid ester "Ryoto sugar ester S-570" (manufactured by Mitsubishi-Kagaku Foods Corporation), 0.1% of sucrose fatty acid ester "Ryoto sugar ester S-1670" (manufactured by Mitsubishi-Kagaku Foods Corporation) and 0.015% of sodium polyphosphate were prepared and pre-emulsified at 60° C. for 15 minutes. The mixture further homogenized under high pressure at 5 Mpa followed by cooling at 5° C. overnight to prepare a soybean-containing whipping cream liquid. To 1 kg of the whipping cream liquid, 70 g of granulated sugar was added and the mixture was whipped by high speed stirring with a Hobart mixer for 2 minutes and 30 seconds. An overrun of the obtained soybean-containing whipped cream was 159.4%. The soybean-containing whipped cream had melting in the mouth with cooling feel and rich taste without taste of raw vegetation peculiar to soybean and received a high overall evaluation.

Comparative Example a1

A soybean-containing whipping cream liquid was prepared in a similar manner of Example a1 except for substituting dispersing liquid obtained by dispersing commercially available soybean emulsion composition "Soy Supreme Kreme" (powder, manufactured by SunOpta Grains and Foods Group) to adjust a dry matter content to 18.2% similar to the soybean emulsion composition B for the soybean emulsion composition B. To 1 kg of the whipping cream liquid, 70 g of granulated sugar was added and the mixture was whipped by high speed stirring with a Hobart mixer for 2 minutes and 50 seconds. An overrun of the obtained soybean-containing whipped cream was 155.0%. The soybean-containing whipped cream had melting in the mouth with cooling feel, but had strongish taste of raw vegetation peculiar to soybean and poor rich taste, and received a low overall evaluation.

Reference Example a1

To 1 kg of fresh cream (fat content: 30%, manufactured by Takanashi Milk co., ltd.) at 5° C., 70 g of granulated sugar was added and the mixture was whipped by high speed stirring with a Hobart mixer for 1 minutes and 30 seconds. An overrun of the obtained whipped cream was 140.0%. The whipped cream had melting in the mouth with cooling feel and good rich and milk taste and received a high overall evaluation.

Result of taste evaluation of Example a1, Comparative Example a1 and Reference Example a1 was shown in table 3. Taste evaluation of the following Examples was obtained by sensory evaluation with 10 panelists and average of evaluation by panelists according to the following evaluation criteria (Evaluation criteria)
−: Not detectable, ±: Almost not detectable, +: Detectable, ++: Slightly strongly detectable, +++: Strongly detectable
⊙: Strong rich taste, without taste of raw vegetation
◯: Rich taste, little taste of raw vegetation
Δ: Weak rich taste, taste of raw vegetation
×: Without rich taste, strong taste of raw vegetation

TABLE 3

| | Rich taste | Taste of raw vegetation | Overall evaluation | Taste evaluation |
|---|---|---|---|---|
| Example a1 | +++ | ± | ⊙ | Rich taste of soybean, very good taste |
| Comparative Example a1 | + | ++ | Δ | Taste of raw vegetation, slightly bud taste |
| Reference Example a1 | +++ | − | ⊙ | Rich milk taste, very good taste |

Example a2

Preparation of Ice Cream

A mixture of 50% of the soybean emulsion composition B prepared in the Production Example 2, 11% of superfine sugar and 8% of honey (sakura-marked pure honey) was prepared and stirred. The mixture was stirred and cooled from 70° C. by using ice cream maker to obtain frozen ice cream liquid. To 69 parts of the liquid, 31 parts of the soybean-containing whipped cream obtained in Example a1 was added and stirred to obtain soy ice cream. Taste of the soy ice cream was evaluated after storing at −20° C. for 15 days. As a result, the soy ice cream had smooth texture with cooling feel in the mouth and rich taste without taste of raw vegetation peculiar to soybean and received a high overall evaluation.

Example a3

A mixture of 50% of the soybean emulsion composition B prepared in the Production Example 2, 11% of superfine sugar, 7% of unrefined sugar and 1% of water was prepared and stirred. The mixture was stirred and cooled from 70° C. by using ice cream maker to obtain frozen ice cream liquid. To 69 parts of the liquid, 31 parts of the soybean-containing whipped cream obtained in Example a1 was added and stirred to obtain soy ice cream. Taste of the soy ice cream was evaluated after storing at −20° C. for 15 days. As a result, the soy ice cream had smooth texture with cooling feel in the mouth and rich taste without taste of raw vegetation peculiar to soybean and received a high overall evaluation.

Comparative Example a2

A frozen ice cream liquid was prepared in a similar manner of Example a2 except for substituting dispersing liquid obtained by dispersing commercially available soybean emulsion composition "Soy Supreme Kreme" (powder, manufactured by SunOpta Grains and Foods Group) to adjust a dry matter content to 18.2% similar to the soybean emulsion composition B for the soybean emulsion composition B. To 69 parts of the liquid, 31 parts of the soybean-containing whipped cream obtained in Comparative Example a1 was added and stirred to obtain soy ice cream. Taste of the soy ice cream was evaluated after storing at −20° C. for 15 days. As a result, the soy ice cream had smooth texture with cooling feel in the mouth, but had strongish taste of raw vegetation peculiar to soybean and poor rich taste, and received a low overall evaluation.

Reference Example a2

A frozen ice cream liquid was prepared in a similar manner of Example a2 except for substituting fresh cream of Reference Example a1 for the soybean emulsion composition B. To 69 parts of the liquid, 31 parts of the soybean-containing whipped cream obtained in Example a1 was added and stirred to obtain ice cream. Taste of the ice cream was evaluated after storing at −20° C. for 15 days. As a result, the ice cream had smooth texture with cooling feel in the mouth and good rich and milk taste and received a high overall evaluation.

Result of taste evaluation of Examples a2-a3, Comparative Example a2 and Reference Example a2 was shown in table 4.

TABLE 4

|  | Rich taste | Taste of raw vegetation | Overall evaluation | Taste evaluation |
| --- | --- | --- | --- | --- |
| Example a2 | +++ | ± | ⊙ | Rich taste of soybean, very good taste |
| Example a3 | +++ | ± | ⊙ | Rich taste of soybean, very good taste |
| Comparative Example a2 | + | ++ | Δ | Taste of raw vegetation, slightly bud taste |
| Reference Example a2 | +++ | − | ⊙ | Rich milk taste, very good taste |

Example a4

Preparation of Cream Soup

A mixture of 30.1% of sweet corn, 6.0% of roasted onion (manufactured by Ebara Foods Industry Inc.), 15.0% of the soybean emulsion composition A prepared in the Production Example 1, 3.0% of superfine sugar, 0.3% of table salt, 0.5% of chicken consomme flavored powder, 0.1% of sodium bicarbonate, 45.1% of water and proper amount of white pepper was prepared and heated to 85° C. by putting the bowl in hot water to prepare cream of corn soup with soymilk. The soup had thickness and smooth texture and rich taste without taste of raw vegetation peculiar to soybean and received a high overall evaluation.

Comparative Example a3

A cream of corn soup with soymilk was prepared in a similar manner of Example a4 except for substituting pure soymilk (solid matter: 6.5%, manufactured by Fuji Oil Co., Ltd.) for the soybean emulsion composition A. The soup had thickness and smooth texture without taste of raw vegetation peculiar to soybean, but had poor rich taste.

Reference Example a3

A cream of corn soup with soymilk was prepared in a similar manner of Example a4 except for substituting fresh cream of Reference Example a1 for the soybean emulsion composition A. The soup had thickness and smooth texture and good rich and milk taste and received a high overall evaluation.

Result of taste evaluation of Example a4, Comparative Example a3 and Reference Example a3 was shown in table 5.

TABLE 5

|  | Rich taste | Taste of raw vegetation | Overall evaluation | Taste evaluation |
| --- | --- | --- | --- | --- |
| Example a4 | +++ | ± | ⊙ | Rich taste of soybean, very good taste |
| Comparative Example a3 | + | ± | Δ | Without rich taste, not enough taste |
| Reference Example a3 | +++ | − | ⊙ | Rich milk taste, very good taste |

Example a5

Milk Pudding-like Soybean-derived Raw Material-containing Food

To 90.81% of the soybean emulsion composition B prepared in the Production Example 2, 9.08% of sugar and 0.11% of brine for tofu (41° Brix) were added and mixed. The mixture was poured into a container and steamed at 95° C. for 25 minutes to obtain milk pudding-like soybean-derived raw material-containing food. The obtained soybean-derived raw material-containing food had smooth texture with some elasticity similar to pudding without taste of raw vegetation peculiar to soybean and received a high overall evaluation.

Example a6

Preparation of Fruit and Milk Beverage-like Soy Beverage

To 68.3% of water, 9.0% of sugar was added and dissolved. To the solution, 17.5% of the soybean emulsion composition B prepared in the Production Example 2 and 5.0% of 2 times concentrated banana juice were added and mixed. The mixture was adjusted to pH 6.0 by adding 50% aqueous solution of citric acid. Then, the mixture was heated to 70° C. and homogenized under high pressure at 15 Mpa and then heating to 93° C. Then, 0.2% of banana flavor was added to the mixture. And then, the mixture was cooled to 20° C. in cold water. The obtained banana flavored beverage had rich taste without taste of raw vegetation peculiar to soybean and received a high overall evaluation.

Example a7

To 78.4% of water, a mixture of 9.0% of sugar and water-soluble soybean polysaccharide "Soyafive S-ZR100" (manufactured by Fuji Oil Co., Ltd.) was added and dissolved at 80° C. for 10 minutes with stirring. The aqueous solution was cooled to 20° C., and 10.2% of the soybean emulsion composition B prepared in the Production Example 2 and 2.0% of 5 times concentrated peach juice were added to the solution and mixed. The mixture was adjusted to pH 3.8 by adding 50% aqueous solution of citric acid. Then, the mixture was heated to 70° C. and homogenized under high pressure at 15 Mpa and then heating to 93° C. Then, 0.1% of peach flavor was added to the mixture. And then, the mixture was cooled to 20° C. in cold water. The obtained peach flavored beverage had rich taste without taste of raw vegetation peculiar to soybean and received a high overall evaluation.

Example a8

Preparation of Cheese Souffle-like Soymilk Soffle (1)

To 200 g of egg yolk in Hobart Mixer Bowl, 30 g of granulated sugar was added and lightly whipped with moderate stirring. Then, 300 g of the soybean emulsion composition B and 80 g of soft wheat flour were sequentially-added while slow stirring. In the last, meringue, which was separately prepared by adding 100 g of granulated sugar and 70 g of trehalose (manufactured by Hayashibara Co., Ltd.) to 220 g of egg white and whipping with stirring, was added and mixed to prepare soy milk souffle dough with specific gravity of 0.29. Then, 600 g of prepared dough was divided into 8 parts and put on wet newspaper and baked in an oven for 18 minutes with opening damper at 190° C. of upper temperature and 160° C. of lower temperature to obtain cheese souffle-like soymilk soffle. The obtained soymilk souffle had soft texture and good melting in the mouth similar to cheese souffle, and rich taste without taste of raw vegetation peculiar to soybean and received a high overall evaluation.

Example a9

Preparation of Cheese Souffle-like Soymilk Soffle (2)

To 280 g of soybean emulsion composition B in Hobart Mixer Bowl, 40 g of egg yolk, 35 g of granulated sugar and 15 g of corn starch were sequentially-added while slow stirring. Then, 320 g of cream cheese-like product (product name: Crème Fromage, manufactured by Fuji Oil Co., Ltd.), 40 g of egg yolk, and 20 g of soft wheat flour were sequentially-added and mixed while slow stirring. In the last, meringue, which was separately prepared by adding 70 g of granulated sugar and 30 g of trehalose (manufactured by Hayashibara Co., Ltd.) to 150 g of egg white and whipping with stirring, was added and mixed to prepare soy milk souffle dough with specific gravity of 0.45. Then, 300 g of prepared dough was poured into aluminum cup with 50 mm of diameter and put on bowl in hot water and then baked in an oven for 30 minutes with opening damper at 180° C. of upper temperature. The obtained cheese souffle-like soymilk souffle had soft texture and good melting in the mouth similar to cheese souffle, and cheese taste and rich taste without taste of raw vegetation peculiar to soybean and received a high overall evaluation.

Specific Examples of the Second Aspect of the Invention

Example b1

Preparation of Acidic Soybean Material (Whey Non-separated Type)

The soybean emulsion composition B obtained in Production Example 2 was used as a raw material for fermentation. And a whey non-separated type acidic soybean material was prepared by subjecting the soybean emulsion composition B to lactic acid fermentation as follows.
To the soybean emulsion composition B adjusted the temperature to 22° C., 0.01 wt % of lactic acid bacterium starter for cheese manufactured by Christian Hansen A/S was added, and this was subjected to fermentation at 22° C. for 8 hours. After the fermentation, sodium hydroxide was added to be pH 5.6, and then heating for pasteurization by boiling to 70° C. while stirring with a spatula.
A taste and physical property of the obtained acidic soybean materials including the following Examples and Comparative Example was evaluated by chosen 5 expert panelists. Result of the evaluation was shown in table 6. The acidic soybean material of this Example had a good taste having rich taste derived from lactic acid fermentation and less bitterness or other unpleasant taste. The physical property was soft paste form similar to that of fromage bran, a type of fresh cheese.

Example b2

Preparation of Acidic Soybean Material (Whey Separated Type)

The soybean emulsion composition B obtained in Production Example 2 was used as a raw material for fermentation. And a whey separated type acidic soybean material was prepared by subjecting the soybean emulsion composition B to lactic acid fermentation as follows.
A lactic acid fermentation, pH adjustment and heat pasteurization were carried out in similar manner of Example b1. Then, whey was separated and removed by using centrifuge and a curd was recovered. The obtained acidic soybean material had appropriate hardness similar to cream cheese and a good taste having rich taste derived from lactic acid fermentation and less bitterness or other unpleasant taste.

Example b3

Preparation of Acidic Soybean Material (Whey Separated Type, Phosphate was Added before Separation)

Lactic acid fermentation was carried out in a similar manner of Example b2. Then 0.2% of sodium polyphosphate was added at the same time of adjusting pH by using sodium hydroxide. And then, heat pasteurization and separation of whey were carried out in a similar manner of Example b2. The obtained acidic soybean material had appropriate hardness similar to cream cheese, reduced coarse texture, and a good taste having rich taste derived from lactic acid fermentation and less bitterness or other unpleasant taste.

Example b4

Preparation of Acidic Soybean Material (Whey Separated Type, Phosphate was Added after Separation)

Lactic acid fermentation, pH adjustment, heat pasteurization and separation of whey were carried out in a similar manner of Example b2. Then, 0.5% of sodium polyphosphate dissolved in a small amount of water was added while kneading with kneader, and then heated to 85° C. to react phosphate and protein. The obtained acidic soybean material had appropriate hardness similar to cream cheese, little coarse texture, and a good taste having rich taste derived from lactic acid fermentation and less bitterness or other unpleasant taste.

Comparative Example b1

Acidic Soybean Material Prepared from Soybean Protein Isolate

Lactic acid fermentation, pH adjustment and heat pasteurization whey were carried out in a similar manner of Example b1 except that 10% solution of soybean protein isolate "Fujipro E" (manufactured by Fuji Oil Co., Ltd.) was used as a raw material for fermentation. The obtained acidic soybean material had acrid coarse texture and significantly bitterness and other unpleasant taste, and was difficult to eat.

Comparative Example b2

Acidic Soybean Material Prepared from Whole Fat Soymilk

Lactic acid fermentation, pH adjustment and heat pasteurization whey were carried out in a similar manner of Example b1 except that whole fat soymilk "pure soymilk" (manufactured by Fuji Oil Co., Ltd.) was used as a raw material for fermentation. The obtained acidic soybean material had acrid coarse texture and significantly bitterness and other unpleasant taste, especially rotting acidic smell, and was difficult to eat.

Comparative Example b3

Acidic Soybean Material Prepared from Commercially Available Soybean Emulsion Composition Lactic acid fermentation, pH adjustment and heat pasteurization whey were carried out in a similar manner of Example b1 except that commercially available soybean emulsion composition "Soy Supreme Kreme" (manufactured by SunOpta Grains and Foods Group) was used as a raw material for fermentation after adding water to adjust solid matter same as the soybean emulsion composition prepared in Production Example 2. The obtained acidic soybean material had acrid coarse texture and significantly bitterness and other unpleasant taste, especially rotting acidic smell, and was difficult to eat.

TABLE 6

| | Whey separation | Adding phosphate | Rich taste | Odor | After-taste | Overall taste | Texture |
|---|---|---|---|---|---|---|---|
| Example b1 | None | None | + | ± | ± | ○ | Δ |
| Example b2 | Done | None | ++ | − | ± | ○ | ○ |
| Example b3 | Done | Before whey separation | ++ | − | ± | ⊙ | ○ |
| Example b4 | Done | After whey separation | ++ | ± | ± | ○ | ⊙ |
| Comparative Example b1 | None | None | ± | ++ | ++ | Δ | X |
| Comparative Example b2 | None | None | ± | +++ | +++ | X | Δ |
| Comparative Example b3 | None | None | + | ++ | ++ | X | Δ |

(Evaluation Criteria)

| Each taste | −: Not detectable, ±: Slightly detectable, +: Detectable, ++: Strongly detectable, +++: More strongly detectable |
|---|---|
| Overall taste | ⊙: Strong rich taste of both soybean and fermentation, and no bad taste |
| | ○: rich taste of soybean and fermentation, and little of bad taste |
| | Δ: A little rich taste, and bad taste |
| | X: Poor rich taste, and strong bad taste |
| Texture evaluation | ⊙: Smooth without coarse texture |
| | ○: Acceptable, but a little coarse texture |
| | Δ: Coarse texture |
| | X: Acrid coarse texture |

Applicative Example b1

No-Bake Cheesecake-like Food

To 350 parts of the acidic soybean material obtained in Example b1, a mixture prepared by mixing 8 parts of powdered gelatin soaked in 40 parts of water, 15 parts of "Soykrema 15" (manufactured by Fuji Oil Co., Ltd.), which is soymilk and soy flour mixed product, and 15 parts of liquid sugar and dissolving with heating was added. Then, 360 parts of soy cream "soy krema whip" (manufactured by Fuji Oil Co., Ltd.) was added after whipping. In the last, meringue, which was prepared by mixing 100 parts of egg white and 100 parts of granulated sugar and whipping, was added and mixed to prepare no-bake cheesecake-like food with specific gravity of about 0.5.

The obtained no-bake cheesecake-like food had a quality comparable to a no-bake cheesecake made from cheese or filled type cheese. In addition, the food has rich taste and freshness and smooth texture derived from soybean.

Applicative Example b2

Baked Cheesecake-like Food

To a mixture of 288 parts of the acidic soybean material obtained in Example b1 and 80 parts of granulated sugar, a mixture obtained by heating cream "Gateau Neue 22" (manufactured by Fuji Oil Co., Ltd.) and adding to 125 parts of white chocolate "Couverture White Cacao" (manufactured by Fuji Oil Co., Ltd.) and fully emulsifying was mixed. And then, a mixture of 32.5 parts of whole egg and 32.5 parts of egg yolk was mixed. In the last, 19.5 parts of corn starch was mixed to prepare dough.

Next, tart pastry "Dur Fairede PS8H" (manufactured by Fuji Oil Co., Ltd.) was baked in oven at 160° C. of upper temperature/160° C. of lower temperature and then crumbed. To this, margarine "message 500" (manufactured by Fuji Oil Co., Ltd.) was mixed after melting by heating. Then, 40 g of the mixture was spread into metal ramequin (diameter 12 cm). Over the mixture, 300 g of the cheese dough prepared from the acidic soybean material was poured. The ramequin was put on sheet pan in which about 40° C. of warm water was poured, and baked in oven at 165° C. of upper temperature/165° C. of lower temperature for 30 minutes and then baked at 190° C. of upper temperature for 5 minutes to obtain baked cheesecake-like food browned on the top.

The obtained baked cheesecake-like food had an appearance comparable to baked cheesecake made from cheese or filled type cheese and rich taste. As for the texture, floury sweet potato-like texture was given and novel cake can be obtained different from conventional baked cheesecake.

Specific Examples of the Third Aspect of the Invention

Examples c1-c2, Comparative Example c1

Applications to Mayonnaise

According to the formulation as shown in the following table 7, mayonnaise formulating the soybean emulsion composition B prepared in the Production Example 2 was prepared by mixing raw materials other than rice vinegar and fat by stirring with a Homomixer, then adding rice vinegar, then adding fat in a few parts while stirring, and then sufficiently stirring. Control formulation was based on a general formulation commonly used for mayonnaise. In addition, egg yolk substitution ratio in Example c1, c2 and Comparative Example c1 was 50, 70 and 53%, respectively.

TABLE 7

Formulation of mayonnaise (%)

|  | Control | Example c1 | Example c2 | Comparative Example c1 |
|---|---|---|---|---|
| Soybean emulsion composition B | — | 7.5 | 14.0 | — |
| Pure soymilk (manufactured by Kikkoman soyfoods Co.) | — | — | — | 8.5 |
| Egg yolk | 15.0 | 7.5 | 6.0 | 7.5 |
| Rapeseed oil | 70.0 | 70.0 | 72.5 | 70.0 |
| Rice vinegar | 10.0 | 10.0 | 6.0 | 10.0 |
| Soybean oil | — | — | — | 0.65 |
| Table salt | 1.5 | 1.5 | 1.5 | 1.5 |
| Water | 3.5 | 3.5 | — | 1.85 |
| (Egg yolk substitution rate) | — | 50% | 70% | 53% |

Result of evaluating viscosity, texture and taste of mayonnaise prepared from each formulation was shown in table 8.

Mayonnaise of Examples c1 and c2 in which 50 to 70% of egg yolk was substituted with the soybean emulsion composition B had viscosity and texture similar to commercially available mayonnaise. In addition, taste was good, creamy and rich taste without taste of raw vegetation.

On the other hand, mayonnaise of Comparative Example c1 showed reduced viscosity and did not have texture similar to mayonnaise. In addition, although there was no taste of raw vegetation, taste was not good, poor rich taste and too weak taste.

TABLE 8

|  | Control | Example c1 | Example c2 | Comparative Example c1 |
|---|---|---|---|---|
| Viscosity (mPa·s) (*1) | Off the scale | 47500 | 45000 | 21000 |
| Texture (*2) (Taste evaluation) | Control | Pass | Pass | Reject |
| Rich taste (*3) | Control | Pass | Pass | Reject |
| Taste of raw vegetation (*4) | — | Pass | Pass | Pass |

(*1) Viscosity: Viscosity was measured by using a BM-type viscometer with rotor No. 4 at 6 rpm for 1 minute.
(*2) Evaluation criteria of texture Pass: Viscosity or viscous property similar to control. Reject: Viscosity or viscous property different from that of control.
(*3) Evaluation criteria of rich taste Pass: Rich taste similar to control. Reject: Insufficient rich taste compared to that of control.
(*4) Evaluation criteria of taste of raw vegetation Pass: No or little taste of raw vegetation. Reject: Taste of raw vegetation.

Example c3

Application to Dressing

To 280 g of water, 3 g of water-soluble soybean polysaccharide (Soyafive-S; manufactured by Fuji Oil Co., Ltd.) was added and dissolved with stirring. Then, 70 g of sugar, 70 g of soy sauce, 10 g of table salt, 160 g of vinegar and 7 g of dried bonito flake extract were added. After sufficient stirring and mixing, 400 g of the soybean emulsion composition B prepared in Production Example 2 was added to adjust total amount of the mixture to 1000 g. The mixture was further homogenized with a Homomixer, then heated to 90° C., and then filled to container to obtain dressing. The obtained dressing had rich and good taste.

Example c4

Application to Baste

A boiled-down mirin (sweet cooking rice wine) was prepared by boiling 100 g of mirin in a pan. Then, 500 g of water and 150 g of soy sauce were added. Once reaching a rolling boil, 20 g of dried bonito flake was added and then the mixture was boiled for a little. Then, boiling was stopped and the mixture was filtered with gauze for removing the dried bonito flake after cooling at room temperature to prepare sauce part.

A mixture of 300 g of the above sauce part and 700 g of the soybean emulsion composition A prepared in Production Example 1 was homogenized with a Homomixer, then heated to 90° C., and then filled to container to obtain baste.

The obtained baste had smooth texture and rich and good taste.

Example c5

Application to Custard-like Food (Containing Maple Syrup)

A mixture of 200 g of the soybean emulsion composition B obtained in Production Example 2, 15 g of soft wheat flour, 15 g of high fructose corn syrup (FC: manufactured by Oji Cornstarch Co., Ltd.), 30 g of superfine sugar, 5 g of oligotose (manufactured by Mitsubishi-Kagaku Foods Corporation), 5 g of maple syrup (Maple Syrup No1 Medium, manufactured by Kyoritsu Foods Co. Inc.) and 45 g of water was prepared and once filtered. The filtered mixture was poured into pan and heated. After boiling, the mixture was kneaded for 5 minutes, and then, water at same amount as evaporated water was added and mixed to obtain a custard-like food containing maple syrup.

The obtained custard-like food had smooth texture and rich and good taste without taste of raw vegetation from soybean.

Comparative Example c2

A custard-like food was prepared in a similar manner of Example c5 except for substituting 200 g of a mixture obtained by mixing "Soy Supreme Kreme" (powder, manufactured by SunOpta Grains and Foods Group) with water to adjust a dry matter content to 18.2% for the soybean emulsion composition B.

The obtained custard-like food had a little rich taste and taste of raw vegetation from soybean, that is, the taste was not good.

Example c6

Application to Custard-like Food (Containing Unrefined Sugar)

A mixture of 200 g of the soybean emulsion composition B obtained in Production Example 2, 15 g of soft wheat flour, 15 g of high fructose corn syrup (FC: manufactured by Oji Cornstarch Co., Ltd.), 32 g of superfine sugar, 5 g of oligotose (manufactured by Mitsubishi-Kagaku Foods Corporation), 5 g of unrefined sugar (manufactured by Ueno Sugar Co., Ltd.) and 48 g of water was prepared and once filtered. The filtered mixture was poured into pan and heated. After boiling, the mixture was kneaded for 5 minutes, and then, water at same amount as evaporated water was added and mixed to obtain a custard-like food containing unrefined sugar.

Example c7

Application to Pudding-like Food

A mixture of 28 g of whole egg, 14 g of sugar and 58 g of the soybean emulsion composition B obtained in Production Example 2 was prepared and heated at 80° C. Then, the mixture was baked in oven (150° C.) with putting on bowl in hot water to prepare a pudding-like food.

The obtained pudding-like food had both good texture and good taste.

Example c8

Application to Bavarois-like Food

A mixture of 92 g of the soybean emulsion composition B obtained in Production Example 2 and 7 g of sugar was prepared and heated at 80° C., and then cooled to 40° C. Then, 1 g of powdered gelatin soaked in a small amount of water was added to the mixture. Then, the mixture was cooled and set in refrigerator for 4 hours to prepare a bavarois-like food.

The obtained bavarois-like food had both good texture and good taste.

Example c9

Application to Brulee-like Food

A mixture of 80 g of the soybean emulsion composition B obtained in Production Example 2, 8 g of sugar and 0.1 g of brine (Brix=41) was prepared and steamed with a steamer at 95° C. for 25 minutes. Then caramelization was carried out to prepare a brulee-like food. The obtained brulee-like food had appropriate hardness, smooth texture and good taste.

Example c10

Application to Carbonara Sauce

A mixture of 52 g of the soybean emulsion composition A obtained in Production Example 1, 25 g of powdered cheese, 15 g of bacon and 0.5 g of baking powder was prepared and mixed to prepare carbonara sauce.

The obtained carbonara sauce had rich and good taste. The sauce was easy to be dressed to pasta and good taste can be obtained when boiled pasta was dressed in the sauce.

Example c11

Application to Chawan-mushi

A mixture of 50 g of the soybean emulsion composition B obtained in Production Example 2, 25 g of egg, 120 g of soup stock and 1 g of table salt was prepared and poured into container. Then, the mixture was steamed with a steamer at 85° C. for 15 minutes to obtain chawan-mushi. The obtained chawan-mushi had appropriate hardness, smooth texture and good taste.

Example c12

Application to Mayonnaise

To the soybean emulsion composition B, transglutaminase (product name: Activa, manufactured by Ajinomoto Co., Inc.) was added at a content of 0.5% relative to the soybean emulsion composition B (2.7% relative to dry matter of the soybean emulsion composition B) and acted at 55° C. for 30 minutes, and then heated at 90° C. for 30 minutes for terminating the reaction to obtain an egg yolk substitute composition with transglutaminase reaction.

A mixture of 40 g of this egg yolk substitute composition, 0.7 g of mustard powder, 3 g of table salt, 0.25 g of sodium glutamate, 8 g of mixed vinegar prepared by mixing apple vinegar and acetic acid where the acid degree was adjusted to 10% and 8 g of water was prepared. Then, 140 g of rapeseed oil was added to the mixture while mixing with food cutter to prepare mayonnaise.

The obtained mayonnaise in which 100% of egg yolk was substituted with egg yolk substitute composition had very good and stable emulsion state and rich and good taste without characteristic taste like pickled soybean.

Example c13

Application to Custard-like Food

Four parts by weight of white chocolate (product name: White Coating YDV36, manufactured by Fuji Oil Co., Ltd.) was melted by putting container in hot water at 50° C. To the white chocolate after moving from hot water, 3 parts by weight of the soybean emulsion composition B obtained in Production Example 2 was gradually added and mixed while gentry stirring to prepare a custard-like food.

The obtained custard-like food had smooth texture and rich and good taste without taste of raw vegetation from soybean.

Specific Examples of the Fourth Aspect of the Invention

Comparative Example d1

Tofu (Control)

To 80 parts of commercially available soymilk (dry matter content: 11%), 0.5 part of brine was added and sufficiently mixed. The mixture was filled into container and steamed with a steamer at 95° C. for 25 minutes. Then, the mixture was naturally cooled to obtain conventional tofu which was traditionally produced.

The obtained tofu was firm but fragile gel and hard to melting in the mouth, and had a texture as broken into pieces by chewing.

Example d1

Tofu 2

To 80 parts of the soybean emulsion composition B obtained in Production Example 2 (dry matter content: 18.2%), 0.1 part of brine was added and sufficiently mixed. The mixture was filled into container and steamed with a steamer at 95° C. for 25 minutes. Then, the mixture was naturally cooled to obtain tofu.

The obtained tofu did not have firm but fragile gel property such as Comparative Example d1, but had a property of soft and easy to spoon out. In addition, the texture was creamy and good melting in the mouth, like a texture of a pudding containing cream with smooth texture or Ankimo (liver of sea toad), which was rich and good melting in the mouth, rather than texture of tofu. In addition, the taste of the obtained tofu was clearly different from that of tofu of Comparative Example d1, and was richer and good soybean taste.

The obtained tofu with putting ponzu soy sauce had a very good taste.

Example d2

Tofu 3

Tofu was prepared in a similar manner of Comparative Example d1 except that 8 parts, 32 parts or 48 parts of soymilk was substituted with the soybean emulsion composition B obtained in Production Example 2 in the formulation of Comparative Example d1. As a result, each tofus with substitution rate of soymilk of 10%, 40% and 60%, respectively, were obtained.

The substitution rate of soymilk was higher, the obtained tofu had richer taste and more creamy texture.

Example d3

Soybean Seasoning

A soybean seasoning was obtained by adding 25 parts of ponzu soy sauce to 75 parts of the soybean emulsion composition B obtained in Production Example 2 and sufficiently mixing. When the seasoning was put on sashimi (sliced raw fish) and eaten, there were creamy and moderately acidic taste and rich taste. The seasoning had appearance and viscosity similar to sesame sauce. The seasoning was excellent with sashimi.

Example d4

Yuba

The soybean emulsion composition B obtained in Production Example 2 was filled into tray with height of 2 cm, and frozen at −20° C. for 10 days in freezer. Flecks of yuba could be obtained by defrosting this. This yuba had a smooth texture and rich taste similar to fresh lifted-up yuba. Taste was further improved by adding seasoning to this yuba.

Reference Example d1

Frozen Tofu (Control)

To 5 kg of whole soybean, 15 kg of water (10° C.) was added and the soybean was immersed for 14 hours. The mixture was separated to immersed whey and immersed soybean with 10 mesh sieve. The immersed soybean and 25 kg of water (20° C.) was ground with a grinder (manufactured by Nagasawa Kikai Seisakusho Co., Ltd., the same will apply hereafter) to prepare "go". The "go" was subjected to separate machine (manufactured by Tofer Co., Ltd., the same will apply hereafter) to separate to soymilk (solid content: 9%) and okara. This soymilk was heated at 98° C. for 5 minutes by using an indirect heating apparatus (manufactured by Hoshitaka Co., Ltd., the same will apply hereafter). The obtained soymilk was adjusted to 12% of solid content in a vacuum of 100 torr with a concentrator (manufactured by Hisaka Works Ltd., the same will apply hereafter) to obtain concentrated soymilk.

Next, the concentrated soymilk was adjusted to 75° C. of temperature. Then, to 100 parts of the concentrated soymilk, 3 parts of waxy corn starch "Delica SE" (manufactured by Nippon Starch Chemical Co., Ltd.), 2 parts of dextrin "Sundec 250" (manufactured by Sanwa Starch Co., Ltd) and 0.9 part of magnesium chloride preparation "Magnesfine TG" (manufactured by Kao Corporation.) was added. Then, the mixture was poured into mold and coagulated. Coagulation temperature was 70° C. After the coagulation, the coagulant was steamed at 90° C. for 40 minutes. It was cooled to 20° C. or less, then cut into predefined size, and then rapidly frozen under about −35° C. atmosphere to obtain frozen tofu (control).

Examples d5, d6

Frozen Tofu

To the concentrated soymilk obtained in Reference Example d1, the soybean emulsion composition B obtained in Production Example 2 (dry matter content 18.2%) was mixed at a ratio of the concentrated soymilk:the soybean emulsion composition=70:30 (Example d5) or 40:60 (Example d6), and then, preparation was carried out in a similar manner of Reference Example d1 to obtain frozen tofu.

Reference Example d2

Frozen Atsu-Age (Control)

Tofu before frozen was prepared in a similar manner of Reference Example d1 except that solid content of the soymilk was adjusted to 16%. This tofu was deep-fried in rapeseed oil at 180° C. for 2 minutes, and then rapidly frozen under about −35° C. atmosphere to obtain frozen atsu-age (control).

Examples d7-d9

Frozen Atsu-age

To the concentrated soymilk obtained in Reference Example d2, the soybean emulsion composition B obtained in Production Example 2 (dry matter content: 18.2%) was mixed at a ratio of the concentrated soymilk:the soybean emulsion composition B=85:15 (Example d7), 70:30 (Example d8) or 40:60 (Example d9), and then, preparation was carried out in a similar manner of Reference Example d1 to obtain tofu before frozen. These tofus were deep-fried with rapeseed oil at 180° C. for 2 minutes, and then rapidly frozen under about −35° C. atmosphere to obtain frozen atsu-age.

(Evaluation Method)

Texture of frozen tofu and atsu-age was evaluated by sensory evaluation after defrosting under room temperature. Frozen tofu having a smooth texture similar to tofu was assumed to be 5 points. Frozen tofu having a hard texture and bad melting in the mouth or having a thickened texture due to addition of starch was assumed to be 1 point. With respect to taste, frozen tofu having pleasant bean taste was assumed to be 5 points. Frozen tofu without bean taste was assumed to be 1 point. Sensory evaluation was carried out by 5 panelists as five-rank evaluation.

TABLE 9

Effect of adding the soybean emulsion composition B to frozen tofu

|  | Reference Example d1 | Example d5 | Example d6 |
|---|---|---|---|
| Substitution ratio of soybean emulsion composition B (relative to soymilk) | 0% | 30% | 60% |
| Texture | 2 | 4 | 5 |
| Taste | 2 | 4 | 5 |

(Evaluation of Frozen Tofu)

In Reference Example d1, taste was bland with a little soybean rich taste. In addition, texture was hard and similar to conventional tofu.

In the case of Example d5, the concentrated soymilk:the soybean emulsion composition B=70:30, full (rich) soybean taste was given compared to Reference Example d1, and taste of raw vegetation was not given. Texture was soft, smooth and good melting in the mouth, and a texture to which grain of the tofu melted when chewing.

In the case of Example d6, the concentrated soymilk:the soybean emulsion composition B=40:60, further richer soybean taste was given than Example d5. Texture was very soft, smooth, creamy and good melting in the mouth like a pudding.

TABLE 10

Effect of adding the soybean emulsion composition B to silken atsu-age

|  | Reference Example d2 | Example d7 | Example d8 | Example d9 |
|---|---|---|---|---|
| Substitution ratio of soybean emulsion composition B (relative to soymilk) | 0% | 15% | 30% | 60% |
| Texture | 2 | 3 | 4 | 5 |
| Taste | 2 | 3 | 4 | 5 |

(Evaluation of Silken Atsu-Age)

In Reference Example d2, taste was bland with a little soybean rich taste. In addition, texture was hard, hard to melting in the mouth and bad melting in the mouth.

In the case of Example d7, the concentrated soymilk:the soybean emulsion composition B=85:15, soybean taste was given compared to Reference Example d2. Texture was changed to soft and smooth from that of Reference Example d2.

In the case of Example d8, the concentrated soymilk:the soybean emulsion composition B=70:30, further richer soybean taste was given than Example d7. Texture was soft and smooth.

In the case of Example d9, the concentrated soymilk:the soybean emulsion composition B=40:60, further richer soybean taste was given than Example d8 and it was preferable. Texture was very soft, very creamy and good melting in the mouth.

From a result of the above Examples d5-d9 and Reference Examples d1, d2, substitution ratio of the soybean emulsion composition B relative to soymilk was preferably 15% or more to obtain sufficient addition effect. More preferably, rich soybean taste and soft and smooth texture could be given in the substitution ratio of 20% or more.

Reference Example d3

Ganmodoki 1 (Control)

As a protein raw material, 450 parts of powdered soybean protein isolate "Fujipro E" (manufactured by Fuji Oil Co., Ltd., the same will apply hereafter), and 360 parts of rapeseed oil and 1420 parts of water were put into silent cutter, then kneaded at about 20° C., and then uniformly emulsified for 3 minutes to obtain an emulsion. To the emulsion, 15 parts of seasoning, 18 parts of okara and 30 parts of wheat flour, and 150 parts of diced carrot and 9 parts of sesame were added and mixed to a dough.

The dough was formed to 58 mm of diameter, 10 mm of thickness and 27 g per one by using a forming machine. This was deep-fried in lower temperature part (92 to 135° C.) for 8 minutes and higher temperature part (155 to 180° C.) for 1 minutes and 30 seconds, then air-cooled, and then rapidly frozen at −35° C. to obtain frozen ganmodoki.

Example d10

Ganmodoki 2 (Containing the Soybean Emulsion Composition B)

Ganmodoki was obtained in a similar manner of Reference Example d3 except that all amount of water was substituted with the soybean emulsion composition B obtained in Production Example 2.

The obtained ganmodoki was bigger size than conventional ganmodoki, and had sponge-like structure internally and novel juicy texture in the mouth with maintaining its volume and absorbing flavor liquid well after boiling. And its taste had rich taste derived from soybean.

Comparative Example d2

Ganmodoki was obtained in a similar manner of Reference Example d3 except that all amount of water was substituted with soymilk from whole soybean (solid content: 9.1%, protein content: 4.7%, fat content: 3.6%).

Comparative Example d3

Ganmodoki was obtained in a similar manner of Reference Example d3 except that all amount of water was substituted with cream for kneading "Milrea" (solid content: 28.4%, fat content: 15.0%, manufactured by Fuji Oil Co., Ltd.).

Examples d11-d14

Ganmodoki 3 (Varying an Additive Amount of the Soybean Emulsion Composition B

Each ganmodoki was obtained in a similar manner of Reference Example d3 except that 142 parts, 355 parts, 710 parts or 1420 parts of the soybean emulsion composition B obtained in Production Example 2 per butch of the dough was added to the dough and water was added so that protein content in the dough was same to obtain each ganmodoki of which substitution rate relative to water was 10%, 25%, 50% or 100% (Example d11, d12, d13, d14). The higher additive amount of the soybean emulsion composition B provided that the obtained ganmodoki maintained its volume after deep-frying and could absorb higher amount of flavored liquid.

(Evaluation Method)

For the obtained ganmodoki, expansion degree was visually observed, and size of long side (X), short side (Y), and thickness (H) was measured with slide gauge, and volume was calculated from average (mm) of 5 products, and expansion condition after deep-frying was observed. The volume (V) was calculated by a math formula, $V \approx R^2 \times 3.14 \times H$, where radius (R cm) was a half of average of long side and short side. Value was shown as a proportion (%) with assuming that a volume of Reference Example 3 was 100.

In addition, the ganmodoki was boiled in Japanese style flavored liquid (2 tablespoons of soy sauce, 4 tablespoons of sugar, 4 teaspoons of mirin, 4 teaspoons of sake and 800 cc of soup stock) for about 15 minutes and took out and measured its weight. And, flavored liquid-absorption rate of ganmodoki was determined as a rate (%) of weight of ganmodoki before boiling to weight of ganmodoki after boiling.

Further, taste, form (expansion) and absorbing property of ganmodoki were evaluated on five rank as (+++): very good, (++): good, (+): slightly good, (±): acceptable, (−): bad.

TABLE 11

| | Reference Example d3 | Example d10 | Comparative Example d2 | Comparative Example d3 |
|---|---|---|---|---|
| Substitution ratio of soybean emulsion composition B relative to water (%) | 0 | 100 | 0 | 0 |
| Taste | ± | +++ Strong rich taste of soybean | + Rich taste of soybean | − A little rich taste of soybean |
| Form (expansion) | ± | +++ | + | + |
| Volume ratio | 100 | 130 | 106 | 105 |
| Absorbing property | ± | +++ | + | + |
| Absorption rate % (before and after boiling) | 180 | 260 | 195 | 206 |

| | Example d11 | Example d12 | Example d13 | Example d14 |
|---|---|---|---|---|
| Substitution ratio of soybean emulsion composition B relative to water (%) | 10 | 25 | 50 | 100 |
| Taste | + Small change | ++ Rich taste of soybean | ++ Rich taste of soybean | +++ Strong rich taste of soybean |
| Form (expansion) | + | + | ++ | +++ |
| Volume ratio | 108 | 114 | 121 | 130 |
| Absorbing property | + | + | ++ | +++ |
| Absorption rate % (before and after boiling) | 205 | 210 | 230 | 260 |

(Evaluation Result)

From Examples d10-d14 and Comparative Examples d2, d3, rough standard of substitution ratio of the soybean emulsion composition B relative to water was preferably 10% or more, more preferably 25% or more to obtain sufficient addition effect. Further preferably, ganmodoki having bigger volume and thicker form after deep-frying could be obtained in the substitution ratio of 50% or more. The obtained ganmodoki had fine sponge-like structure internally and juicy texture in the mouth with absorbing flavor liquid well after boiling.

Reference Example d4

Abura-age 1 (Control)

Five hundred parts of powdered soybean protein isolate, 60 parts of fat (palm oil), 1550 parts of water, 25 parts of corn starch and 5 parts of table salt were put into silent cutter, then kneaded at about 20° C., and then uniformly emulsified for 3 minutes to obtain an emulsion. To the emulsion, 12 parts of magnesium chloride dissolved in 15 parts of water was added and mixed for 1 minute to prepare a dough having appropriate hardness.

The dough was formed to 66.5×46 mm and 15.5 g per one by using a forming machine. This was deep-fried with a three-stage fryer (at 70° C. for 4 minutes, at 110° C. for 2 minutes, at 170° C. for 4 minutes) with using 100×77 mm size of mold form to obtain abura-age.

Example d15

Aburaage 2 (Containing the Soybean Emulsion Composition B)

Abura-age was obtained in a similar manner of Reference Example d4 except that 760 parts of 1550 parts of water was substituted with the soybean emulsion composition B obtained in Production Example 2.

The obtained abura-age had puffy appearance and fine internal structure. In addition, it had richer taste derived from soybean than conventional abura-age. Further, juicy flavored abura-age well absorbing flavored liquid was obtained in the case of adding taste with flavored liquid.

When this abura-age was dried by heating after deliquoring to weight ratio of abura-age to flavored liquid to 1:1, abura-age having volume (thickness) same as before flavoring was obtained. The flavored dried abura-age which showed good reconstruction property by hot water and included flavored liquid was obtained.

Comparative Example d4

Abura-age was obtained in a similar manner of Reference Example d4 except that 760 parts of 1550 parts of water was substituted with soymilk from whole soybean (solid content 9.1%, protein content 4.7%, fat content 3.6%).

Comparative Example d5

Abura-age was obtained in a similar manner of Reference Example d4 except that 760 parts of 1550 parts of water was substituted with cream for kneading "Milrea" (solid content 28.4%, fat content 15.0%, manufactured by Fuji Oil Co., Ltd.).

Examples d16-d19

Abura-Age 3 (Varying an Additive Amount of the Soybean Emulsion Composition B)

Each abura-age was obtained in a similar manner of Reference Example d4 except that soybean protein isolate was 500 parts and rapeseed oil was 60 parts, and that 150 parts, 380 parts, 760 parts or 1525 parts of the soybean emulsion composition B obtained in Production Example 2 per butch of the dough was added to the dough and water was added so that protein content in the dough was same to obtain each aburaage of which substitution rate relative to water was 10%, 25%, 50% or 85% (Examples d16, d17, d18, d19).

(Evaluation method)

For the obtained abura-age, expansion degree was visually observed, and size of long side, short side, and thickness was measured with slide gauge, and volume was calculated from average (mm) of 5 products, and expansion condition after deep-frying was observed. Value was shown as a proportion (%) with assuming that a volume of Reference Example 4 was 100.

In addition, the abura-age was boiled in Japanese style flavored liquid for about 3 minutes and took out and measured its weight. And, flavored liquid-absorption rate of abura-age was determined as a rate (%) of weight of abura-age before boiling to weight of abura-age after boiling.

Further, taste, form (expansion) and absorbing property of abura-age were evaluated on five rank as (+++): very good, (++): good, (+): slightly good, (±): acceptable, (−): bad.

TABLE 12

|  | Reference Example d4 | Example d15 | Comparative Example d4 | Comparative Example d5 |
|---|---|---|---|---|
| Substitution ratio of soybean emulsion composition B relative to water (%) | 0 | 50 | 0 | 0 |
| Taste | ± | ++ Rich taste of soybean | + Taste of soybean | − A little taste of soybean |
| Form (expansion) | ± | ++ | + | ± |
| Volume ratio | 100 | 138 | 106 | 98 |
| Absorbing property | ± | ++ | + | ± |
| Absorption rate % (before and after boiling) | 230 | 320 | 245 | 97 |

|  | Example d16 | Example d17 | Example d18 | Example d19 |
|---|---|---|---|---|
| Substitution ratio of soybean emulsion composition B relative to water (%) | 10 | 25 | 50 | 100 |
| Taste | + Taste of soybean | ++ Rich taste of soybean | ++ Rich taste of soybean | +++ Strong rich taste of soybean |
| Form (expansion) | + | + | ++ | +++ |
| Volume ratio | 108 | 126 | 138 | 156 |
| Absorbing property | + | + | ++ | +++ |
| Absorption rate % (before and after boiling) | 260 | 270 | 320 | 350 |

(Evaluation Result)

From Examples d15-d19 and Comparative Examples d4, d5, rough standard of substitution ratio of the soybean emulsion composition B relative to water was preferably 10% or more, more preferably 25% or more to obtain sufficient addition effect. Further preferably, abura-age having bigger volume and thicker form after deep-frying could be obtained in the substitution ratio of 50% or more. The obtained abura-age had fine sponge-like structure internally and juicy texture in the mouth with absorbing flavor liquid well after boiling.

Specific Examples of the Fifth Aspect of the Invention

Example e1, Comparative Example e1

Serum Cholesterol Reducing Test

Serum cholesterol was measured after feeding a feed having formulation as shown in table 13 to rat.

TABLE 13

| Feed formulation g/100 g feed formulation CP20% | | |
|---|---|---|
| Components | Comparative Example e1 | Example e1 |
| Casein | 22.7 | 11.4 |
| Soybean emulsion composition B | — | 33.3 |
| Soybean oil (*) | 20.0 | 0.0 |
| β-corn starch | 24.3 | 22.4 |
| sucrose | 10.0 | 10.0 |
| α-corn starch | 13.2 | 13.2 |
| Cellulose | 5.0 | 5.0 |
| Mineral mix (AIN-93G) | 3.5 | 3.5 |
| Vitamin mix (AIN-93) | 1.0 | 1.0 |
| Choline bitartrate (mL) | 0.3 | 0.3 |
| Total | 100 | 100 |

(*) contains 0.002% TBHQ

Note)
Two feeds having same protein content and fat content was prepared by adjusting crude protein content (CP) in the feed = 10% from casein + 10% from sample and adjusting fat content by adding soybean oil to supplement insufficient amount of fat according to fat content of "soybean emulsion composition B"-containing feed (20%).

Test Method

Animal: Zucker fatty rat

Number of animal, period: n=6×2 groups, 2 weeks

Test sample: Casein, soybean emulsion composition B

Procedure: <Body weight, intake> Measured every day
<Blood sampling> Total 2 times (Interim, at final anatomy)

Analysis: <About cholesterol> Serum cholesterol level (Fuji Dri-Chem)

Test Result

As for the serum cholesterol level, experimental plot of using the soybean emulsion composition B (Example e1) showed significantly lower value than experimental plot of using casein (Comparative Example e1) after 2 weeks feeding. The serum cholesterol level in the rat at the time of starting test was 144.7+4.7 mg/dl (mean value±SE). It is known that Zucker fatty rat is a mutant that shows remarkable obesity, and that the serum cholesterol level rises with aging.

It was shown that rise of the serum cholesterol level according to aging of Zucker fatty rat positively suppressed in Example e1 while rise of serum cholesterol level according to aging of Zucker fatty rat was not any suppressed by casein-containing feed in Comparative Example e1.

Example f1, Comparative Example f1

Urinary NAG Activity Reducing Test

Urinary NAG (β-N-acetyl-D-glucosaminidase) was measured after feeding a feed having formulation as shown in table 14 to rat. Damage such as degeneration or destruction of renal tubular epithelial cell can be found by determining urinary NAG level because NAG in serum is hard to pass into urine due to its remarkably large size while NAG is widely distributed in internal organs.

TABLE 14

Feed formulation
g/100 g feed formulation CP20%

| Components | Comparative Example f1 | Example f1 |
|---|---|---|
| Casein | 22.7 | 11.4 |
| Soybean emulsion composition B | — | 33.3 |
| Soybean oil (*) | 20.0 | 0.0 |
| β-corn starch | 24.3 | 22.4 |
| sucrose | 10.0 | 10.0 |
| α-corn starch | 13.2 | 13.2 |
| Cellulose | 5.0 | 5.0 |
| Mineral mix (AIN-93G) | 3.5 | 3.5 |
| Vitamin mix (AIN-93) | 1.0 | 1.0 |
| Choline bitartrate (mL) | 0.3 | 0.3 |
| Total | 100 | 100 |

(*) contains 0.002% TBHQ

Test Method
Animal: Zucker fatty rat
Number of animal, period: n=6×2 groups, 2 weeks
Test sample: Casein, soybean emulsion composition B
Procedure: <Body weight, intake> Measured every day
<Blood sampling> Total 2 times (Interim, at final anatomy)
Analysis: Urinary NAG activity (NAG test Shionogi), urinary protein (Tonein-TP)

Test Result

As for the urinary NAG activity, experimental plot of using the soybean emulsion composition B showed significantly lower value than experimental plot of using casein after 2 weeks feeding. It is known that the Zucker fatty rat is a mutant which shows remarkable obesity, and that nephropathy is developed with aging as coexisting illness.

It was shown that development of nephropathy according to aging of Zucker fatty rat positively suppressed in Example e1 while development of nephropathy according to aging of Zucker fatty rat was not any suppressed by casein-containing feed in Comparative Example e1.

Industrial Applicability

The first aspect to fifth aspect of the invention can be used for producing various foods in which soybean derived raw material is used as a raw material for various purposes.

For example, in a production of confectionery, bread, dessert, beverage, soup, sauce or the like, a soybean-derived raw material-containing food or beverage which has significantly improved taste can be provided by substituting the soybean emulsion composition of the first aspect of the invention which has significantly improved taste for a part or all of dairy product such as milk, fresh cream and powdered whole fat milk.

In addition, for example, consumers can reduce their serum cholesterol or can improve their renal function through dietary habit by using a composition for reducing serum cholesterol or improving renal function according to the fifth aspect of the invention. Thus, it becomes possible to develop a product that stimulates new demand in the food industry.

The invention claimed is:

1. A soybean extracted food or beverage emulsion which is obtained by adding water to a fat containing soybean comprising a fat at a content of 35 wt % or more in terms of dry basis and having a Nitrogen Solubility Index in the range from 20 to 77 to prepare a suspension liquid, and then subjecting the suspension liquid to a solid-liquid separation to transfer neutral lipid and polar lipid to an insoluble fraction, and then removing a soluble fraction comprising protein and sugar, and then recovering the insoluble fraction which comprises the soybean extracted food or beverage emulsion, wherein the soybean emulsion has a protein content of 25 wt % or more in terms of dry basis, a fat content 100 wt % or more relative to the protein content in terms of dry basis, a fiber content of 10 wt % or less, a lipophilic proteins content index value of 55% or more, and contains a denatured lipophilic protein.

2. An acidic soybean material obtained by acidification of the soybean extracted food or beverage emulsion of claim 1 with a lactic acid bacteria.

3. A dairy product substitution or a fermented dairy product substitution comprising the soybean extracted food or beverage emulsion of claim 1 or the acidic soybean material of claim 2.

4. The soybean extracted food or beverage emulsion of claim 1, which has an lipophilic proteins content of 60% or more.

5. The soybean extracted food or beverage emulsion of claim 1, which comprises a fat at a content of 120 to 250 wt % relative to the protein content.

6. An egg yolk substitute composition comprising the soybean extracted food or beverage emulsion composition of claim 1.

7. An egg yolk substitute composition comprising the soybean extracted food or beverage emulsion of claim 2.

8. An egg yolk substitute food comprising the egg yolk substitute composition of claim 6 as a partial or complete substitute for an egg yolk.

9. A processed soy food comprising the soybean extracted food or beverage emulsion composition of claim 1 as a part or all of a soybean raw material of the processed soy food.

10. A processed soy food comprising the soybean extracted food or beverage emulsion composition of claim 2 as a part or all of a soybean raw material of the processed soy food.

11. A composition for reducing serum cholesterol or improving renal function, comprising the soybean emulsion composition of claim 1.

12. A composition for reducing serum cholesterol or improving renal function, comprising the soybean emulsion composition of claim 2.

13. A food comprising the composition for reducing serum cholesterol or improving renal function of claim 11.

* * * * *